United States Patent

Manka et al.

[11] Patent Number: 6,001,783
[45] Date of Patent: Dec. 14, 1999

[54] MIXED POLYSULFIDES AND LUBRICANTS AND FUNCTIONAL FLUIDS CONTAINING THE SAME

[75] Inventors: John S. Manka, Euclid; William D. Abraham, South Euclid; Stephen H. Roby, Chesterland; James A. Supp, Parma; Richard Yodice, Mentor, all of Ohio

[73] Assignee: The Lubrizol Corporation, Wickliffe, Ohio

[21] Appl. No.: 08/823,467

[22] Filed: Mar. 24, 1997

[51] Int. Cl.$^6$ ............... C10M 137/10; C10M 137/14
[52] U.S. Cl. ............ 508/428; 508/430; 508/272; 508/273; 508/274
[58] Field of Search ............... 548/112; 508/272, 508/273, 274, 276, 428, 430

[56] References Cited

U.S. PATENT DOCUMENTS

| | | | |
|---|---|---|---|
| 2,694,682 | 11/1954 | Harle | 252/33.6 |
| 2,719,827 | 10/1955 | Lowe | 252/47 |
| 2,743,235 | 4/1956 | McDermott | 252/46.7 |
| 2,905,639 | 9/1959 | Krzikalla et al. | 508/273 |
| 3,094,548 | 6/1963 | Price et al. | 260/461 |
| 3,197,405 | 7/1965 | LeSuer | 508/349 |
| 3,281,507 | 10/1966 | Price et al. | 260/968 |
| 3,770,854 | 11/1973 | Morris et al. | 260/985 |
| 3,844,963 | 10/1974 | Elliott et al. | 508/428 |
| 3,904,619 | 9/1975 | D'Amico | 260/246 |
| 3,914,241 | 10/1975 | Elliott et al. | 508/273 |
| 3,980,573 | 9/1976 | Okorodudu | 508/274 |
| 4,017,168 | 4/1977 | Okorodudu | 260/302 |
| 4,039,552 | 8/1977 | Brois et al. | 285/8 |
| 4,188,299 | 2/1980 | Caspari | 508/274 |
| 4,234,435 | 11/1980 | Meinhardt et al. | 252/51.5 A |
| 4,417,990 | 11/1983 | Clason et al. | 252/32.7 E |
| 4,501,679 | 2/1985 | Reierson et al. | 252/77 |
| 4,562,259 | 12/1985 | Theobald et al. | 548/112 |
| 4,755,311 | 7/1988 | Burjes et al. | 508/188 |
| 4,758,362 | 7/1988 | Butke | 508/221 |
| 5,002,674 | 3/1991 | Farng et al. | 252/32.7 |
| 5,256,321 | 10/1993 | Todd | 252/32.7 E |

FOREIGN PATENT DOCUMENTS 937361  9/1963  United Kingdom .

OTHER PUBLICATIONS

Kato et al., "A Convenient Synthesis of Novel Unsymmetrical Acyl Thioacyl Disulfides and Acyl O,O–Dialkylthiophosphoryl Disulfides," *Synthesis*, 1981, No. 5 pp. 370–371.

Kato et al., "Thioacylsulfenyl Bromides: Electrolytic dithiocarboxylating Reagents," *Tetrahedron Letters*, 27 (38), 1986, pp. 4594–4598.

Boreca et al., "Synthesis and Chemical Properties of Dialkoxyoxophosphoranesulfenates," Bull. Acad. Pol. Sci., Ser. Sci. Chem, 22 (3) 1974, pp. 201–205.

*Primary Examiner*—Jerry D. Johnson
*Attorney, Agent, or Firm*—David M. Shold

[57] ABSTRACT

This invention relates to a composition, comprising:

(A) at least one compound selected from the group consisting of (A-1) a compound represented by the formula $$T^1T^2-P(X^1)-(S)_n-S-C(X^2)-L^1 \quad \text{(A-I)}$$

(A-2) a compound represented by the formula $$T^3T^4-P(X^3)-(S)_n-S-(DMTD)-S-J \quad \text{(A-II)}$$

(A-3) a compound represented by the formula $$L^2-C(X^4)-(S)_n-S-(DMTD)-S-G \quad \text{(A-III)}$$

and (A-4) mixture of two or more of (A-1), (A-2) and (A-3);

wherein in Formulae (A-I), (A-II) and (A-III): (DMTD) is a dimercaptothiadiazole nucleus; J is H, SR, $-S-P(X^5)-T^5T^6$ or $-S-C(X^6)-L^3$ G is H, SR or $-S-C(X^7)-L^4$ $T^1$, $T^2$, $T^3$, $T^4$, $T^5$ and $T^6$ are independently R, SR or OR; $L^1$, $L^2$, $L^3$ and $L^4$ are independently R, SR, OR or NRR; $X^1$, $X^2$, $X^3$, $X^4$, $X^5$, $X^6$ and $X^7$ are independently O or S; each R is independently a hydrocarbyl group; and n is 1 to 4. In one embodiment, the inventive composition further comprises (B) an acylated nitrogen-containing compound having a substituent of at least about 10 aliphatic carbon atoms, (C) a phosphorus compound, (D) a thiocarbamate, and/or (E) an organic sulfide other than (A). The invention also relates to a lubricating composition or functional fluid characterized by enhanced antiwear properties and comprising the foregoing component (A) and, optionally, one or more of the foregoing components (B), (C), (D) and/or (E).

29 Claims, No Drawings

MIXED POLYSULFIDES AND LUBRICANTS AND FUNCTIONAL FLUIDS CONTAINING THE SAME

TECHNICAL FIELD

This invention relates to certain mixed polysulfides, and to lubricants and functional fluids containing such mixed polysulfides. The lubricants and functional fluids are characterized by enhanced antiwear properties.

BACKGROUND OF THE INVENTION

Engine lubricating oils require the presence of additives to protect the engine from wear. For almost 40 years, the principal antiwear additive for engine lubricating oils has been zinc dialkyl dithiophosphate (ZDDP). However, ZDDP is typically used in the lubricating oil at a sufficient concentration to provide a phosphorus content of 0.12% by weight or higher in order to pass required industry standard tests for antiwear. Since phosphates may result in the deactivation of emission control catalysts used in automotive exhaust systems, a reduction in the amount of phosphorus-containing additives (e.g., ZDDP) in the oil would be desirable. The problem sought to be overcome is to provide for a reduction in the amount of phosphorus-containing additive in the lubricating oil and yet provide the lubricating oil with desired antiwear properties. The present invention provides a solution to this problem by providing compositions that can function as either a partial or complete replacement for ZDDP.

The use of ashless dispersants in lubricants is disclosed in numerous patents, including U.S. Pat. Nos. 3,172,892; 3,219,666; 3,272,746; 3,310,492; 3,341,542; 3,444,170; 3,455,831; 3,455,832; 3,576,743; 3,630,904; 3,632,511; 3,804,763; and 4,234,435.

The use of metal salts of phosphorodithioic acids as additives for lubricants is disclosed in U.S. Pat. Nos. 4,263,150; 4,289,635; 4,308,154; 4,322,479; and 4,417,990. Amine salts of such acids are disclosed as being useful as additives for grease compositions in U.S. Pat. No. 5,256,321.

U.S. Pat. No. 4,758,362 discloses the addition of a carbamate to a low phosphorus or phosphorus free lubricating oil composition to provide a composition with enhanced extreme-pressure and antiwear properties.

The use of disulfides represented by the formula $(R_zYC=S)_2S_2$, wherein Y is O, S or N, and z is 1 when Y is O or S and 2 when Y is N, as lubricant additives is disclosed in U.S. Pat. Nos. 2,681,316; 2,691,632; and 2,694,682.

U.S. Pat. No. 2,307,307 discloses the use of compounds represented by the formula $(RXC=S)_2S_n$, wherein X is O or S, and n is greater than 2, as lubricant additives.

The use of compounds represented by the formula $(ROC=S)S_2$ in lubricants for use on bearing surfaces is disclosed in U.S. Pat. Nos. 2,110,281 and 2,206,245. U.S. Pat. No. 2,431,010 discloses the use of compounds represented by the formula $(ROC=S)S_n$, wherein n is 2–4, as soluble cutting oil additives.

The use of thiuram sulfides as lubricant additives is disclosed in U.S. Pat. Nos. 2,081,886; 2,201,258; 3,249,542; 3,352,781; 4,207,196; and 4,501,678.

U.S. Pat. No. 5,034,141 discloses that improved antiwear results can be obtained by combining a thiodixanthogen (e.g., octylthiodixanthogen) with a metal thiophosphate (e.g., ZDDP). U.S. Pat. No. 5,034,142 discloses the addition of a metal alkoxyalkylxanthate (e.g., nickel ethoxyethylxanthate), a dixanthogen (e.g., diethoxyethyl dixanthogen) and a metal thiophosphate (e.g., ZDDP) to a lubricant to improve antiwear.

European patent application 0 609 623 A1 discloses an engine oil composition containing a metal-containing detergent, zinc dithiophosphate, a boron-containing ashless dispersant, aliphatic amide compound, and either a dithiocarbamate compound or an ester derived from a fatty acid and boric acid. Among the dithiocarbamates that are disclosed are sulfides and disulfides.

SUMMARY OF THE INVENTION

This invention relates to a composition, comprising:

(A) at least one compound selected from the group consisting of (A-1) a compound represented by the formula

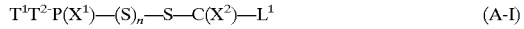  (A-I)

(A-2) a compound represented by the formula

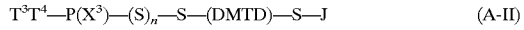  (A-II)

(A-3) a compound represented by the formula

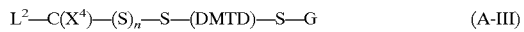  (A-III)

and (A-4) mixture of two or more of (A-1), (A-2) and (A-3); wherein in Formulae (A-I), (A-II) and (A-III):

(DMTD) is a dimercaptothiadiazole nucleus;
J is H, SR, —S—P $(X^5)$—$T^5T^6$ or —S—C $(X^6)$—$L^3$;
G is H, SR or —S—C $(X^7)$—$L^4$;
$T^1$, $T^2$, $T^3$, $T^4$, $T^5$ and $T^6$ are independently R, SR or OR;
$L^1$, $L^2$, $L^3$ and $L^4$ are independently R, SR, OR or NRR;
$X^1$, $X^2$, $X^3$, $X^4$, $X^5$, $X^6$ and $X^7$ are independently O or S;
each R is independently a hydrocarbyl group; and
n is 1 to 4.

In one embodiment, the inventive composition further comprises (B) an acylated nitrogen-containing compound having a substituent of at least about 10 aliphatic carbon atoms. In one embodiment, the inventive composition further comprises (C) a phosphorus compound. In one embodiment, the inventive composition further comprises (D) a thiocarbamate. In one embodiment, the inventive composition further comprises (E) an organic sulfide. In one embodiment, the inventive compositions are lubricating compositions or functional fluids characterized by enhanced antiwear properties and comprising the foregoing component (A) and, optionally, one or more of the foregoing components (B), (C), (D) and/or (E). In one embodiment, the invention relates to a process comprising mixing the foregoing component (A) with an oil of lubricating viscosity and, optionally, one or more of the foregoing components (B), (C), (D) and/or (E).

In one embodiment, the inventive lubricating compositions and functional fluids are characterized by reduced phosphorus levels when compared to those in the prior art, and yet have sufficient antiwear properties to pass industry standard tests for antiwear. The inventive lubricating compositions and functional fluids are especially suitable for use as engine lubricating oil compositions, gear oil compositions and grease compositions.

DESCRIPTION OF THE PREFERRED EMBODIMENTS

As used in this specification and in the appended claims, the terms "hydrocarbyl" and "hydrocarbon based" denote a group having a carbon atom directly attached to the remainder of the molecule and having a hydrocarbon or predominantly hydrocarbon character within the context of this invention. Such groups include the following:

(1) Hydrocarbon groups; that is, aliphatic, (e.g., alkyl or alkenyl), alicyclic (e.g., cycloalkyl or cycloalkenyl), aromatic, aliphatic- and al cyclic-substituted aromatic, aromatic-substituted aliphatic and alicyclic groups, and the like, as well as cyclic groups wherein the ring is completed through another portion of the molecule (that is, any two indicated substituents may together form an alicyclic group). Such groups are known to those skilled in the art. Examples include methyl, ethyl, octyl, decyl, octadecyl, cyclohexyl, phenyl, etc.

(2) Substituted hydrocarbon groups; that is, groups containing non-hydrocarbon substituents which, in the context of this invention, do not alter the predominantly hydrocarbon character of the group. Those skilled in the art will be aware of suitable substituents. Examples include halo, hydroxy, nitro, cyano, alkoxy, acyl, etc.

(3) Hetero groups; that is, groups which, while predominantly hydrocarbon in character within the context of this invention, contain atoms other than carbon in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbyl group.

Terms such as "alkyl-based," "aryl-based," and the like have meanings analogous to the above with respect to alkyl groups, aryl groups and the like.

The term "hydrocarbon-based" has the same meaning and can be used interchangeably with the term hydrocarbyl when referring to molecular groups having a carbon atom attached directly to the remainder of a molecule.

The term "lower" as used herein in conjunction with terms such as hydrocarbyl, alkyl, alkenyl, alkoxy, and the like, is intended to describe such groups which contain a total of up to 7 carbon atoms.

The term "oil-soluble" refers to a material that is soluble in mineral oil to the extent of at least about one gram per liter at 25° C.

(A) Mixed Polysulfides

The compounds (A) are mixed polysulfides. These compounds are selected from the group consisting of (A-1) a compound represented by the formula

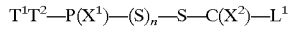   (A-I)

(A-2) a compound represented by the formula

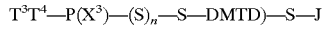   (A-II)

(A-3) a compound represented by the formula

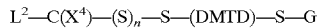   (A-III)

and (A-4) mixture of two or more of (A-1), (A-2) and (A-3). In Formulae (A-I), (A-II) and (A-III), the notation "(DMTD)" refers to a thiadiazole nucleus of dimercaptothiadiazole. J is H, SR, —S—P ($X^5$)—$T^5T^6$ or —S—C ($X^7$)—$L^3$;

G is H, SR or —S—C ($X^7$)—$L^4$ $T^1$, $T^2$, $T^3$, $T^4$, $T^5$ and $T^6$ are independently R, SR or OR. $L^1$, $L^2$, $L^3$ and $L^4$ are independently R, SR, OR or NRR. $X^1$, $X^2$, $X^3$, $X^4$, $X^5$, $X^6$ and $X^7$ are independently O or S. Each R is independently a hydrocarbyl group. n is 1 to 4, and in one embodiment 1 or 2, and in one embodiment n is 1.

The di-mercaptothiadiazole nucleus, (DMTD), utilized in Formulae (A-II) or (A-III) has one or more of the structures:

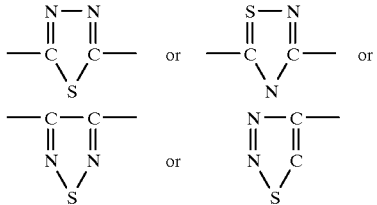

In a preferred embodiment, (DMTD) has the structure:

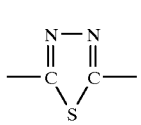

The R groups in Formulae (A-I), (A-II) and (A-III) are hydrocarbyl groups of sufficient length to provide the compounds with a measure of oil solubility. When two or more R groups are present in a single compound, the total number of carbon atoms should be sufficient to provide the compound with such solubility. Generally, each R group will have 1 to about 50 carbon atoms, and in one embodiment 1 to about 30 carbon atoms, and in one embodiment 1 to about 18 carbon atoms, and in one embodiment 1 to about 12 carbon atoms, and in one embodiment 1 to about 8 carbon atoms. Examples of R groups that can be used include methyl, ethyl, propyl, isopropyl, butyl, n-butyl, isobutyl, amyl, 4-methyl-2-pentyl, ethyl hexyl, octyl, isooctyl, decyl, dodecyl, tetradecyl, 2-pentenyl, dodecenyl, phenyl, naphthyl, alkylphenyl, alkylnaphthyl, phenylalkyl, naphthylalkyl, alkylphenylalkyl, alkylnaphthylalkyl, and mixtures thereof.

In one embodiment, component (A) is a compound represented by Formula (A-I), and $T^1$ and $T^2$ are each OR, $X^1$ is S, and n is 1 or 2. In one embodiment, $T^1$ and $T^2$ are each SR, $X^1$ is S, and n is 1 or 2. In one embodiment, $X^2$ is S, $L^1$ is SR, and n is 1 or 2. In one embodiment, $X^2$ is S, $L^1$ is OR, and n is 1 or 2. In one embodiment, $X^2$ is S, $L^1$ is NRR, and n is 1 or 2.

Specific compounds of the type represented by Formula (A-I) are disclosed in the following Table I.

TABLE I $T^1$ $T^2$-P $(X^1)$—$(S)_n$—S—C$(X^2)$-$L^1$ (A-I)

| $T^1$ | $T^2$ | $X^1$ | n | $X^2$ | $L^1$ |
|---|---|---|---|---|---|
| RO | RO | S | 1 | S | OR |
| RO | RO | S | 1 | S | SR |
| RO | RO | S | 1 | S | NRR |
| RO | RO | S | 1 | S | R |
| RS | RS | S | 1 | O | OR |
| RS | RS | S | 1 | O | SR |
| RS | RS | S | 1 | O | NRR |
| RS | RS | S | 1 | O | R |
| RO | RO | O | 1 | S | OR |
| RO | RO | O | 1 | S | SR |
| RO | RO | O | 1 | S | NRR |
| RO | RO | O | 1 | O | OR |
| RO | RO | O | 1 | O | SR |

TABLE I-continued $T^1 T^2-P (X^1)—(S)_n—S—C(X^2)-L^1$ (A-I)

| $T^1$ | $T^2$ | $X^1$ | n | $X^2$ | $L^1$ |
|---|---|---|---|---|---|
| RO | RO | O | 1 | O | NRR |
| RS | RO | S | 1 | S | OR |
| RS | RO | S | 1 | S | SR |
| RS | RO | S | 1 | S | NRR |

Each R is independently isopropyl, butyl, n-butyl, isobutyl, amyl, 4-methyl-2-pentyl, ethylhexyl, octyl, isooctyl, decyl, dodecyl, tetradecyl, 2-pentenyl, dodecenyl, phenyl or naphthyl.

In one embodiment, component (A) is a compound represented by the formula:

$$T^1T^2—P(S)—S—S—C(S)—L^1 \quad (A-IA)$$

wherein in Formula (A-IA), $T^1$ and $T^2$ are the same or different and each is SR or OR, $L^1$ is SR, OR, or NRR, and each R is independently a hydrocarbyl group.

In one embodiment, component (A) is a compound represented by Formula (A-II), and $T^3$ and $T^4$ are each OR, $X^3$ is S, and n is 1 or 2. In one embodiment, n is 1 or 2 and J is H or —S—C $(X^6)$—$L^3$.

In one embodiment, n is 1 or 2 and J is —S—P $(X^5)$—$T^5T^6$.

In one embodiment, n is 1, $T^3$ and $T^4$ are independently OR, $X^3$ is S, and J is SR. In one embodiment, n is 1, $T^3$ and $T^4$ are independently OR, $X^3$ is S, and J is H or —S—C $(X^6)$—$L^3$.

In one embodiment, n is 1, $T^3$ and $T^4$ are independently OR, $X^3$ is S, and J is H or —S—P $(X^5)$—$T^5T^6$.

Specific compounds of the type represented by Formula (A-II) are disclosed in the following Table II.

TABLE II $T^3 T^4-P (X^3)—(S)_n—S-(DMTD)-S-J$ (A-II)

| $T^3$ | $T^4$ | $X^3$ | n | J |
|---|---|---|---|---|
| RO | RO | S | 1 | H |
| RO | RO | S | 1 | SR |
| RO | RO | S | 1 | S—C(=S)OR |
| RO | RO | S | 1 | S—P(=S)(OR)$_2$ |
| RO | RO | O | 1 | H |
| RO | RO | O | 1 | SR |
| RO | RO | O | 1 | S—C(=S)OR |
| RO | RO | O | 1 | S—P(=S)(OR)$_2$ |
| RS | RO | S | 1 | H |
| RS | RO | O | 1 | H |
| RS | RO | S | 1 | S—C(=S)OR |
| RS | RO | S | 1 | S—P(=S)(R)$_2$ |
| RS | RO | O | 1 | S—C(=S)OR |
| RS | RO | O | 1 | S—P(=S)(OR)$_2$ |
| RO | RO | S | 1 | S—C(=S)SR |
| RO | RO | S | 1 | S—P(=S)(SR)$_2$ |

Each R is independently isopropyl, butyl, n-butyl, isobutyl, amyl, 4-methyl-2-pentyl, ethylhexyl, octyl, isooctyl, decyl, dodecyl, tetradecyl, 2-pentenyl, dodecenyl, phenyl or naphthyl.
With each of the foregoing compounds, (DMTD) has the following structural formula:

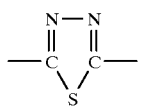

In one embodiment, component (A) is a compound represented by the formula

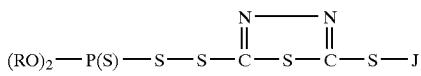

wherein in Formula (A-IIA), J is H or —S—P (S)—(O—R)$_2$ and each R is independently a hydrocarbyl group. In one embodiment, J is H, —S—C (S)—S—R, —S—C (S)—O—R, or —S—C (S)—NRR and each R is independently a hydrocarbyl group.

In one embodiment, component (A) is a compound represented by Formula (A-III), and n is 1 or 2, $T^6$ is SR, $X^4$ is S, and G is H or —S—C $(X^7)$—$T^{10}$.

In one embodiment, n is 1 or 2, $L^2$ is OR, $X^4$ is S, and G is H or —S—C $(X^7)$—$L^4$.

In one embodiment, n is 1, $L^2$ is SR or OR, $X^4$ is S, and G is H or —S—C $(X^7)$—$L^4$.

In one embodiment, n is 1, $L^2$ is SR or OR, $X^4$ is S, and G is SR.

Specific compounds of the type represented by Formula (A-III) are disclosed in the following Table III.

TABLE III $L^2—C(X^4)-(S)_n—S—(DMTD)—S—G$ (A-III)

| $L^2$ | $X^4$ | n | G |
|---|---|---|---|
| RO | S | 1 | H |
| RO | S | 1 | SR |
| RO | S | 1 | SC(=S)R |
| RO | S | 1 | SC(=S)SR |
| RO | 5 | 1 | SC(=S)OR |
| RO | 5 | 1 | SC(=S)NRR |
| RS | 5 | 1 | H |
| RS | 5 | 1 | SR |
| RS | 5 | 1 | SC(=S)R |
| RS | S | 1 | SC(=S)SR |
| RS | S | 1 | SC(=S)OR |
| RS | S | 1 | SC(=S)NRR |
| RO | O | 1 | H |
| RO | O | 1 | SR |
| RO | O | 1 | SC(=S)R |
| RO | O | 1 | SC(=S)SR |
| RO | O | 1 | SC(=S)OR |
| RO | O | 1 | SC(=S)NRR |

Each R is independently isopropyl, butyl, n-butyl, isobutyl, amyl, 4-methyl-2-pentyl, ethylhexyl, octyl, isooctyl, decyl, dodecyl, tetradecyl, 2-pentenyl, dodecenyl, phenyl or naphthyl. With each of the foregoing compounds, (DMTD) has the following structural formula:

In one embodiment, component (A) is a compound represented by the formula

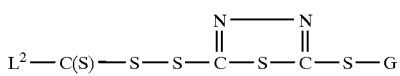

wherein Formula (A-IIIA), $L^2$ is SR, OR or NRR, and G is H, SR, —S—C (S)—S—R, —S—C (S)—O—R, or —S—C (S)—NRR and each R is independently a hydrocarbyl group.

The compounds represented by Formula (A-I) can be prepared by combining an appropriate halogenated hydrocarbon, mercaptan, alcohol or amine with an alkali metal reagent (e.g., NaOH, KOH), and a phosphorus-containing acid represented by the formula $$T^1T^2\text{—}P(X^1)\text{—}SH \qquad (P\text{-}1)$$

wherein in Formula (P-1), $T^1$, $T^2$ and $X^1$ are the same as in Formula (A-I). The resulting mixture is reacted with carbon disulfide and then an oxidizing agent (e.g., hydrogen peroxide, cobalt maleonitriledithioate, $K_2Fe(CN)_6$, $FeCl_3$, dimethylsulfoxide, dithiobis(thioformate), copper sulfate, etc.), sulfur dichloride or sulfur monochloride to form the desired polysulfide compound. The oxygen-containing analogs of these compounds wherein $X^1$ and $X^2$ in Formula (A-I) are oxygen can be prepared by treating the sulfur-containing compounds with water or steam.

When J is —S—P $(X^5)$—$T^5T^6$ in Formula (A-II), the compounds represented by such Formula (A-II) can be prepared by reacting a phosphorus-containing acid represented by the formula $$T^3T^4\text{—}P(X^3)\text{—}SH \qquad (P\text{-}2)$$

wherein in Formula (P-2), $T^3$, $T^4$ and $X^3$ are the same as in Formula (A-II), a phosphorus-containing acid represented by the formula $$T^5T^6\text{—}P(X^5)\text{—}SH \qquad (P\text{-}3)$$

wherein in Formula (P-3), $T^5$, $T^6$ and $X^5$ are the same as in Formula (A-II), and a dimercaptothiadiazole with an oxidizing agent (e.g., hydrogen peroxide, cobalt maleonitriledithioate, $K_2Fe(CN)_6$, $FeCl_3$, dimethylsulfoxide, dithiobis(thioformate), copper sulfate, etc), sulfur dichloride or sulfur monochloride to form the desired polysulfide compound. The phosphorus-containing acids represented by the Formulae (P-2) and (P-3) can be the same or different and preferably are the same. The oxygen-containing analogs of these compounds wherein $X^3$ and $X^5$ in Formula (A-II)are oxygen can be prepared by treating the sulfur-containing compounds with water or steam.

When J is —S—C $(X^6)$—$L^3$ in Formula (A-II), the compounds represented by such Formula (A-II) can be prepared by combining a dimercaptothiadiazole, an appropriate halogenated hydrocarbon, mercaptan, alcohol or amine, an alkali metal reagent (e.g., NaOH, KOH), and a phosphorus-containing acid represented by the formula $$T^3T^4\text{—}P(X^3)\text{—}SH \qquad (P\text{-}2)$$

wherein in Formula (P-2), $T^3$, $T^4$ and $X^3$ are the same as in Formula (A-II). The resulting mixture is reacted with carbon disulfide and then an oxidizing agent (e.g., hydrogen peroxide, cobalt maleonitriledithioate, $K_2Fe(CN)_6$, $FeCl_3$, dimethylsulfoxide, dithiobis(thioformate), copper sulfate, etc.), sulfur dichloride or sulfur monochloride to form the desired polysulfide compound. The oxygen-containing analogs of these compounds wherein $X^3$ and $X^6$ in Formula (A-II) are oxygen can be prepared by treating the sulfur-containing compounds with water or steam.

When J is SR in Formula (A-II), the compounds represented by such Formula (A-II) can be prepared by combining a dimercaptothiadiazole, an appropriate mercaptan, an alkali metal reagent (e.g., NaOH, KOH), and a phosphorus-containing acid represented by the formula $$T^3T^4\text{—}P(X^3)\text{—}SH \qquad (P\text{-}2)$$

wherein in Formula (P-2), $T^3$, $T^4$ and $X^3$ are the same as in Formula (A-II). The resulting mixture is reacted with an oxidizing agent (e.g., hydrogen peroxide, cobalt maleonitriledithioate, $K_2Fe(CN)_6$, $FeCl_3$, dimethylsulfoxide, dithiobis(thioformate), copper sulfate, etc.), sulfur dichloride or sulfur monochloride to form the desired polysulfide compound. The oxygen-containing analogs of these compounds wherein $X^3$ in Formula (A-II)is oxygen can be prepared by treating the sulfur-containing compounds with water or steam.

When J is H in Formula (A-II), the compounds represented by such Formula (A-II)can be prepared by combining a dimercaptothiadiazole, an alkali metal reagent (e.g., NaOH, KOH), and a phosphorus-containing acid represented by the formula $$T^3T^4\text{—}P(X^3)\text{—}SH \qquad (P\text{-}2)$$

wherein in Formula (P-2), $T^3$, $T^4$ and $X^3$ are the same as in Formula (A-II). The resulting mixture is reacted with an oxidizing agent (e.g., hydrogen peroxide, cobalt maleonitriledithioate, $K_2Fe(CN)_6$, $FeCl_3$, dimethylsulfoxide, dithiobis(thioformate), copper sulfate, etc.), sulfur dichloride or sulfur monochloride to form the desired polysulfide compound. The oxygen-containing analogs of these compounds wherein $X^3$ in Formula (A-II)is oxygen can be prepared by treating the sulfur-containing compounds with water or steam.

The compounds represented by Formula (A-III) can be prepared by combining an appropriate halogenated hydrocarbon, mercaptan, alcohol or amine with an alkali metal reagent (e.g., NaOH, KOH), and a dimercaptothiadiazole and reacting the resulting mixture with an oxidizing agent (e.g., hydrogen peroxide, cobalt maleonitriledithioate, $K_2Fe(CN)_6$, $FeCl_3$, dimethylsulfoxide, dithiobis (thioformate), copper sulfate, etc), sulfur dichloride or sulfur monochloride to form the desired polysulfide compound. The oxygen-containing analogs of these compounds wherein $X^4$ and $X^7$ in Formula (A-III) are oxygen can be prepared by treating the sulfur-containing compounds with water or steam.

The phosphorus-containing acids represented by the Formulae (P-1), (P-2) and (P-3) are known in the art. The acids wherein $X^1$, $X^3$ and $X^5$, respectively, are sulfur and $T^1$ and and $T^2$, and $T^3$ and $T^4$, and $T^5$ and $T^6$, respectively, are OR, can be obtained by the reaction of phosphorus pentasulfide ($P_2S_5$) and an alcohol or mixture of alcohols corresponding to $T^1$ and $T^2$, $T^3$ and $T^4$, or $T^5$ and $T^6$, respectively. The reaction involves mixing at a temperature of about 20° C. to about 200° C., four moles of alcohol with one mole of phosphorus pentasulfide. Hydrogen sulfide is liberated in this reaction. The oxygen-containing analogs of these compounds can be prepared by treating the dithioic acid with water or steam.

The halogenated hydrocarbons that can be used to prepare the compounds represented by Formulae (A-I), (A-II)or (A-III) include chlorinated or brominated hydrocarbons of 1 to about 50 carbon atoms, and in one embodiment 1 to about 30 carbon atoms, and in one embodiment 1 to about 18 carbon atoms, and in one embodiment 1 to about 12 carbon atoms, and in one embodiment 1 to about 8 carbon atoms. Specific examples include the methyl, ethyl, propyl, isopropyl, butyl, n-butyl, isobutyl, amyl, 4-methyl-2-pentyl, octyl, isooctyl, decyl, dodecyl, tetradecyl, 2-pentenyl, dodecenyl, phenyl, naphthyl, alkylphenyl, alkylnaphthyl, phenylalkyl, naphthylalkyl, alkylphenylalkyl and alkylnaphtylalkyl chlorides and bromides.

The mercaptans that can be used include the hydrocarbyl mercaptans represented by the formula R—S—H, wherein R is as defined above in Formulae (A-I), (A-II)or (A-III). In one embodiment, R is an alkyl, an alkenyl, cycloalkyl, or cycloalkenyl group. R may be an aryl (e.g., phenyl, naphthyl), alkylaryl, arylalkyl or alkylaryl alkyl group. R may also be a haloalkyl, hydroxyalkyl, or hydroxyalkyl-substituted (e.g., hydroxymethyl, hydroxyethyl, etc.) aliphatic group. In one embodiment, R contains from about 2 to about 30 carbon atoms, or from about 2 to about 24, or from about 3 to about 18 carbon atoms. Examples include butyl mercaptan, amyl mercaptan, hexyl mercaptan, octyl mercaptan, 6-hydroxymethyloctanethiol, nonyl mercaptan, decyl mercaptan, 10-amino-dodecanethiol, dodecyl mercaptan, 10-hydroxymethyl-tetradecanethiol, and tetradecyl mercaptan.

Alcohols used to prepare the compounds of Formulae (A-I), (A-II) or (A-III) include isopropyl, n-butyl, isobutyl, amyl, 4-methyl-2-pentyl, hexyl, isooctyl, decyl, dodecyl, tetradecyl, 2-pentenyl, dodecenyl, aromatic alcohols such as the phenols, etc. Higher synthetic monohydric alcohols of the type formed by Oxo process (e.g., 2-ethylhexyl), the Aldol condensation, or by organo- aluminum catalyzed oligomerization of alpha-olefins (especially ethylene), followed by oxidation and hydrolysis, also are useful. Examples of useful monohydric alcohols and alcohol mixtures include the commercially available "Alfol" alcohols marketed by Continental Oil Corporation. Alfol 810 is a mixture of alcohols containing primarily straight chain, primary alcohols having from 8 to 10 carbon atoms. Alfol 12 is a mixture of alcohols containing mostly $C_{12}$ fatty alcohols. Alfol 1218 is a mixture of synthetic, primary, straight-chain alcohols containing primarily 12 to 18 carbon atoms. The Alfol 20+ alcohols are mixtures of $C_{18}$–$C_{28}$ primary alcohols having mostly, on an alcohol basis, $C_{20}$ alcohols as determined by GLC (gas-liquid-chromatography). The Alfol 22+ alcohols are $C_{18}$–$C_{28}$ primary alcohols containing primarily, on an alcohol basis, $C_{22}$ alcohols. These Alfol alcohols can contain a fairly large percentage (up to 40% by weight) of paraffinic compounds which can be removed before the reaction if desired.

Another example of a commercially available alcohol mixture is Adol 60 which comprises about 75% by weight of a straight chain $C_{22}$ primary alcohol, about 15% of a $C_{20}$ primary alcohol and about 8% of $C_{18}$ and $C_{24}$ alcohols. Adol 320 comprises predominantly oleyl alcohol. The Adol alcohols are marketed by Ashland Chemical.

A variety of mixtures of monohydric fatty alcohols derived from naturally occurring triglycerides and ranging in chain length of from $C_8$ to $C_{18}$ are available from Proctor & Gamble Company. These mixtures contain various amounts of fatty alcohols containing mainly 12, 14, 16, or 18 carbon atoms. For example, CO-1214 is a fatty alcohol mixture containing 0.5% of $C_{10}$ alcohol, 66.0% of $C_{12}$ alcohol, 26.0% of $C_{14}$ alcohol and 6.5% of $C_{16}$ alcohol.

Another group of commercially available mixtures include the "Neodol" products available from Shell Chemical Co. For example, Neodol 23 is a mixture of $C_{12}$ and $C_{13}$ alcohols; Neodol 25 is a mixture of $C_{12}$ and $C_{15}$ alcohols; and Neodol 45 is a mixture of $C_{14}$ to $C_{15}$ linear alcohols. Neodol 91 is a mixture of $C_9$, $C_{10}$ and $C_{11}$ alcohols.

Fatty vicinal diols also are useful and these include those available from Ashland Oil under the general trade designation Adol 114 and Adol 158. The former is derived from a straight chain alpha olefin fraction of $C_{11}$–$C_{14}$, and the latter is derived from a $C_{15}$–$C_{18}$ fraction.

The amines that can be used in making the compounds of Formulae (A-I), (A-II)or (A-III) may be primary, secondary or tertiary amines, or mixtures thereof. Hydrocarbyl groups of the amines may be aliphatic, cycloaliphatic or aromatic. These include alkyl and alkenyl groups. In one embodiment the amine is an alkylamine wherein the alkyl group contains from 1 to about 50 carbon atoms, and in one embodiment 1 to about 30 carbon atoms, and in one embodiment 1 to about 18 carbon atoms, and in one embodiment 1 to about 12 carbon atoms, and in one embodiment 1 to about 8 carbon atoms.

In one embodiment, the amines are primary hydrocarbyl amines containing from about 2 to about 30, and in one embodiment about 4 to about 20 carbon atoms in the hydrocarbyl group. The hydrocarbyl group may be saturated or unsaturated. Representative examples of primary saturated amines are the alkylamines such as methylamine, n-butylamine, n-hexylamine; those known as aliphatic primary fatty amines, for example, the commercially known "Armeen" primary amines (products available from Akzo Chemicals, Chicago, Ill.). Typical fatty amines include amines such as, n-octylamine, n-dodecylamine, n-etradecylamine, n-octadecylamine (stearylamine), octadecenylamine (oleylamine), etc. Also suitable are mixed fatty amines such as Akzo's Armeen-C, Armeen-O, Armeen-OD, Armeen-T, Armeen-HT, Armeen S and Armeen SD, all of which are fatty amines of varying purity.

In one embodiment, the amine is a tertiary-aliphatic primary amine having from about 4 to about 30, and in one embodiment about 6 to about 24, and in one embodiment about 8 to about 24 carbon atoms in the aliphatic group. Usually the tertiary-aliphatic primary amines are monoamines, and in one embodiment alkylamines represented by the formula

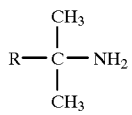

wherein R is a hydrocarbyl group containing from 1 to about 30 carbon atoms. Such amines are illustrated by tertiary-butylamine, 1-methyl-1-amino-cyclohexane, tertiary-octyl primary amine, tertiary-tetradecyl primary amine, tertiary-hexadecyl primary amine, tertiary-octadecyl primary amine, tertiary-octacosanyl primary amine.

Mixtures of tertiary alkyl primary amines are also useful for the purposes of this invention. Illustrative of amine mixtures of this type are "Primene 81R" which is a mixture of $C_{11-14}$ tertiary alkyl primary amines and "Primene JMT" which is a similar mixture of $C_{18-22}$ tertiary alkyl primary amines (both are available from Rohm and Haas). The tertiary alkyl primary amines and methods for their preparation are known to those of ordinary skill in the art. The tertiary-alkyl primary amine useful for the purposes of this invention and methods for their preparation are described in U.S. Pat. No. 2,945,749 which is hereby incorporated by reference for its teachings in this regard.

Primary amines in which the hydrocarbyl group comprises olefinic unsaturation also are useful. Thus, the hydrocarbyl groups may contain one or more olefinic unsaturation depending on the length of the chain, usually no more than one double bond per 10 carbon atoms. Representative amines are dodecenylamine, oleylamine and linoleylamine. Such unsaturated amines are available under the Armeen tradename.

Secondary amines include dialkylamines having two of the above hydrocarbyl, preferably alkyl or alkenyl groups described for primary amines including such commercial fatty secondary amines as Armeen 2C and Armeen HT, and also mixed dialkylamines wherein, for example, one alkyl group is a fatty group and the other alkyl group may be a lower alkyl group (1–7 carbon atoms) such as ethyl, butyl, etc., or the other hydrocarbyl group may be an alkyl group bearing other non-reactive or polar substituents (CN, alkyl, carbalkoxy, amide, ether, thioether, halo, sulfoxide, sulfone) such that the essentially hydrocarbon character of the group is not destroyed.

Tertiary amines such as trialkyl or trialkenyl amines and those containing a mixture of alkyl and alkenyl amines are useful. The alkyl and alkenyl groups are substantially as described above for primary and secondary amines.

Other useful primary amines are the primary etheramines represented by the formula R"OR'NH$_2$ wherein R' is a divalent alkylene group having 2 to about 6 carbon atoms and R" is a hydrocarbyl group of about 5 to about 150 carbon atoms. These primary etheramines are generally prepared by the reaction of an alcohol R"OH wherein R" is as defined hereinabove with an unsaturated nitrile. Typically, the alcohol is a linear or branched aliphatic alcohol with R" having up to about 50 carbon atoms, and in one embodiment up to about 26 carbon atoms, and in one embodiment from about 6 to about 20 carbon atoms. The nitrile reactant can have from about 2 to about 6 carbon atoms, with acrylonitrile being useful. Etheramines are commercially available under the name SURFAM marketed by Mars Chemical Company, Atlanta, Ga. Typical of such amines are those having a molecular weight of from about 150 to about 400. Useful etheramines are exemplified by those identified as SURFAM P14B (decyloxypropylamine), SURFAM P16A (linear C$_{16}$), SURFAM P17B (tridecyloxypropylamine). The hydrocarbyl chain lengths (i.e., C$_{14}$, etc.) of the SURFAM described above and used hereinafter are approximate and include the oxygen ether linkage. For example, a C$_{14}$ SURFAM amine would have the following general formula

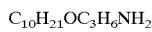
C$_{10}$H$_{21}$OC$_3$H$_6$NH$_2$

The amines may be hydroxyamines. In one embodiment, these hydroxyamines can be represented by the formula

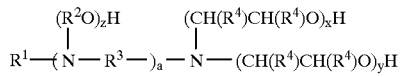

wherein R$^1$ is a hydrocarbyl group generally containing from about 6 to about 30 carbon atoms, R$^2$ is an ethylene or propylene group, R$^3$ is an alkylene group containing up to about 5 carbon atoms, a is zero or one, each R$^4$ is hydrogen or a lower alkyl group, and x, y and z are each independently integers from zero to about 10, at least one of x, y and z being at least 1. The above hydroxyamines can be prepared by techniques well known in the art, and many such hydroxyamines are commercially available. Useful hydroxyamines where in the above formula a is zero include 2-hydroxyethylhexylamine, 2-hydroxyethyloleylamine, bis(2-hydroxyethyl)hexylamine, bis(2-hydroxyethyl) oleylamine, and mixtures thereof. Also included are the comparable members wherein in the above formula at least one of x and y is at least 2.

A number of hydroxyamines wherein a is zero are available from Armak under the general trade designation "Ethomeen" and "Propomeen." Specific examples include "Ethomeen C/15" which is an ethylene oxide condensate of a coconut fatty amine containing about 5 moles of ethylene oxide; "Ethomeen C/20" and "C/25" which also are ethylene oxide condensation products from coconut fatty amine containing about 10 and 15 moles of ethylene oxide, respectively. "Propomeen O/12" is the condensation product of one mole of oleylamine with 2 moles propylene oxide.

Commercially available examples of alkoxylated amines where a is 1 include "Ethoduomeen T/13" and "T/20" which are ethylene oxide condensation products of N-tallow trimethylenediamine containing 3 and 10 moles of ethylene oxide per mole of diamine, respectively.

The fatty diamines include mono- or dialkyl, symmetrical or asymmetrical ethylenediamines, propanediamines (1,2 or 1,3) and polyamine analogs of the above. Suitable fatty polyamines such as those sold under the name Duomeen are commercially available diamines described in Product Data Bulletin No. 7–10R$_1$ of Armak. In another embodiment, the secondary amines may be cyclic amines such as piperidine, piperazine, morpholine, etc.

Also included as useful amines are the following:

(1) polyalkylenepolyamines of the general formula

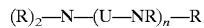
(R)$_2$—N—(U—NR)$_n$—R wherein each R is independently a hydrogen atom or a hydrocarbyl group or a hydroxy-substituted hydrocarbyl group containing up to about 30 carbon atoms, with the proviso that at least one R is a hydrogen atom, n is a number of 1 to about 10, and U is an alkylene group containing 1 to about 18 carbon atoms;

(2) heterocyclic-substituted polyamines including hydroxyalkyl-substituted polyamines wherein the polyamines are as described above and the heterocyclic substituent is, e.g., a piperazine, an imidazoline, a pyrimidine, a morpholine, etc.; and (3) aromatic polyamines of the general formula

Ar—(NR$_2$)$_y$ wherein Ar is an aromatic nucleus of 6 to about 20 carbon atoms, each R is independently a hydrogen atom or a hydrocarbyl group or a hydroxy-substituted hydrocarbyl group containing up to about 30 carbon atoms, with proviso that at least one R$^3$ is a hydrogen atom, and y is 2 to about 8. Specific examples of the polyalkylenepolyamines (1) are ethylenediamine, tetra(ethylene)pentamine, tri-(trimethylene)tetramine, 1,2-propylenediamine, etc. Specific examples of hydroxyalkyl-substituted polyamines include N-(2-hydroxyethyl) ethylenediamine, N, N$^1$-bis(2-hydroxyethyl) ethylenediamine, N-(3-hydroxybutyl) tetramethylenediamine, etc. Specific examples of the heterocyclic-substituted polyamines (2) are N-2-aminoethylpiperazine, N-2 and N-3 aminopropylmorpholine, N-3-(dimethyl amino) propylpiperazine, 2-heptyl-3-(2-aminopropyl)imidazoline, 1,4-bis(2-aminoethyl)piperazine, 1-(2-hydroxyethyl) piperazine, and 2-heptadecyl-1-(2-hydroxyethyl)-imidazoline, etc. Specific examples of the aromatic polyamines (3) are the various isomeric phenylenediamines, the various isomeric naphthalenediamines, etc.

The dimercaptothiadiazoles which can be utilized in making the compounds represented by Formulae (A-II) and (A-III) have the following structural formulae and names.

2,5-Dimercapto-1,3,4-thiadiazole

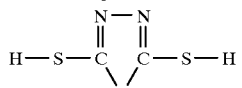

3,5-Dimercapto-1,2,4-thiadiazole

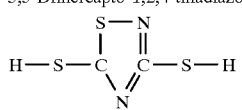

-continued 3,4-Dimercapto-1,2,5-thiadiazole

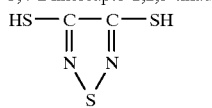

4,5-Dimercapto-1,2,3-thiadiazole

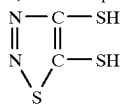

These compounds are known in the art. Of these the most readily available, and the one preferred for the purposes of this invention, is 2,5-dimercapto-1,3,4-thiadiazole. This compound can be prepared by the reaction of one mole of hydrazine, or a hydrazine salt, with two moles of carbon disulfide in an alkaline medium, followed by acidification.

The following examples illustrate the preparation of the mixed polysulfides (A) that are useful with this invention. In the following examples as well as throughout the specification and in the claims, unless otherwise indicated, all parts and percentages are by weight, all temperatures are in degrees Celsius, and the pressures are atmospheric.

EXAMPLE A-1

The following ingredients are charged to a reactor: 2 moles (80 grams) of NaOH; 80 grams of distilled water; and 1 mole (74 grams) of n-butanol. 1.1 moles (84 grams) of carbon disulfide are added dropwise over 30 minutes. One equivalent (346 grams) of dimethypentyl dithiophosphoric acid is added dropwise. The reaction mixture exotherms. The mixture is stirred for 30 minutes. The mixture is cooled in a cold water bath and 2 moles (200 grams) of a 34% hydrogen peroxide solution are added dropwise over 4 hours. The mixture exotherms. The mixture contains an organic layer and an aqueous/solids layer. The organic layer is separated from the aqueous/solids layer. The aqueous/solids layer is washed with 200 ml. of toluene three times to extract product in the form of a toluene extract from the aqueous/solids layer. The organic layer and the toluene extract are combined, stripped on a rotary evaporator at 20 mm Hg and 110° C., and filtered to provide the desired disulfide product.

EXAMPLE A-2

The following ingredients are charged to a reactor: 2 moles (80 grams) of NaOH; 80 grams of distilled water; and 1 mole (129 grams) of di-n-butylamine. 1.1 moles (84 grams) of carbon disulfide are added dropwise over 30 minutes. One equivalent (346 grams) of dimethypentyl dithiophosphoric acid is added dropwise. The reaction mixture exotherms. The mixture is stirred for 30 minutes. The mixture is cooled in a cold water bath and 2 moles (200 grams) of a 34% hydrogen peroxide solution are added dropwise over 4 hours. The mixture exotherms. The mixture contains an organic layer and an aqueous/solids layer. The organic layer is separated from the aqueous/solids layer. The aqueous/solids layer is washed with 200 ml. of toluene three times to extract product in the form of a toluene extract from the aqueous/solids layer. The organic layer and the toluene extract are combined, stripped on a rotary evaporator at 20 mm. Hg and 110° C., and filtered to provide the desired disulfide product.

EXAMPLE A-3

The following ingredients are charged to a reactor: 2 moles (80 grams) of NaOH; 80 grams of distilled water; and 1 mole (74 grams) of 1-butanethiol. 1.1 moles (84 grams) of carbon disulfide are added dropwise over 30 minutes with stirring. One equivalent (346 grams) of dimethypentyl dithiophosphoric acid is added dropwise. The reaction mixture exotherms. The mixture is stirred for 30 minutes. The mixture is cooled in a cold water bath and 2 moles (200 grams) of a 34% hydrogen peroxide solution are added dropwise over 4 hours. The mixture exotherms. The mixture contains an organic layer and an aqueous/solids layer. The organic layer is separated from the aqueous/solids layer. The aqueous/solids layer is washed with 200 ml. of toluene three times to extract product in the form of a toluene extract from the aqueous/solids layer. The organic layer and the toluene extract are combined, stripped on a rotary evaporator at 2 mm. Hg and 110° C., and filtered to provide the desired disulfide product.

EXAMPLE A-4

A phosphorodithioic acid derived from $P_2S_5$ and an alcohol mixture of 40% by weight isopropyl alcohol and 60% by weight 4-methyl-secondary-amyl alcohol (305 grams, 1.0 equivalent) and 2,5-dimercapto-1,3,4-thiadiazole (75 grams, 0.5 equivalents) are charged to a reactor. A 34% aqueous hydrogen peroxide solution (110 grams, 1.1 equivalents) is added dropwise while maintaining the temperature of the reaction mixture at 78–100° C. The reaction mixture is allowed to stand and the mixture separates into two layers. The aqueous layer is drawn off and the remaining organic layer is stripped at 110° C. and 20 mm Hg for two hours. The stripped organic layer is filtered using a filter aid to provide the desired product which is in the form of a yellow liquid.

EXAMPLE A-5

A phosphorodithioic acid derived from $P_2S_5$ and ethyl hexyl alcohol (400 grams, 1.02 equivalents) and 2,5-dimercapto-1,3,4-thiadiazole (30.6 grams, 0.3 equivalent) are charged to a reactor. A 34% aqueous hydrogen peroxide solution (75 grams, 0.75 equivalents) is added while permitting the reaction mixture to reach its reflux temperature (100° C.). The mixture is stripped at 100° C. and 20 mm Hg and filtered to provide the desired disulfide product which is in the form of a yellow liquid.

(B) Acylated Nitrogen-Containing Compounds

In one embodiment, the inventive composition further comprises an acylated nitrogen-containing compound having a substituent of at least about 10 aliphatic carbon atoms. These compounds typically function as ashless dispersants in lubricating compositions.

A number of acylated, nitrogen-containing compounds having a substituent of at least about 10 aliphatic carbon atoms and made by reacting a carboxylic acid acylating agent with an amino compound are known to those skilled in the art. In such compositions the acylating agent is linked to the amino compound through an imido, amido, amidine or salt linkage. The substituent of at least about 10 aliphatic carbon atoms may be in either the carboxylic acid acylating agent derived portion of the molecule or in the amino compound derived portion of the molecule. Preferably, however, it is in the acylating agent portion. The acylating agent can vary from formic acid and its acyl derivatives to acylating agents having high molecular weight aliphatic substituents of up to about 5,000, 10,000 or 20,000 carbon atoms. The amino compounds are characterized by the presence within their structure of at least one HN< group.

In one embodiment, the acylating agent will be a mono- or polycarboxylic acid (or reactive equivalent thereof) such as a substituted succinic or propionic acid and the amino compound is a polyamine or mixture of polyamines, most typically, a mixture of ethylene polyamines. The amine also may be a hydroxyalkyl-substituted polyamine. The aliphatic substituent in such acylating agents typically averages at least about 30 or at least about 50 and up to about 400 carbon atoms.

Illustrative hydrocarbon based groups containing at least 10 carbon atoms are n-decyl, n-dodecyl, tetrapropylene, n-octadecyl, oleyl, chlorooctadecyl, triicontanyl, etc. Generally, the hydrocarbon-based substituents are made from homo- or interpolymers (e.g., copolymers, terpolymers) of mono- and di-olefins having 2 to 10 carbon atoms, such as ethylene, propylene, 1-butene, isobutene, butadiene, isoprene, 1-hexene, 1-octene, etc. Typically, these olefins are 1-monoolefins. The substituent can also be derived from the halogenated (e.g., chlorinated or brominated) analogs of such homo- or interpolymers. The substituent can, however, be made from other sources, such as monomeric high molecular weight alkenes (e.g., 1-tetracontene) and chlorinated analogs and hydrochlorinated analogs thereof, aliphatic petroleum fractions, particularly paraffin waxes and cracked and chlorinated analogs and hydrochlorinated analogs thereof, white oils, synthetic alkenes such as those produced by the Ziegler-Natta process (e.g., poly(ethylene) greases) and other sources known to those skilled in the art. Any unsaturation in the substituent may be reduced or eliminated by hydrogenation according to procedures known in the art.

The hydrocarbon-based substituents are substantially saturated, that is, they contain no more than one carbon-to-carbon unsaturated bond for every ten carbon-to-carbon single bonds present. Usually, they contain no more than one carbon-to-carbon non-aromatic unsaturated bond for every 50 carbon-to-carbon bonds present.

The hydrocarbon-based substituents are also substantially aliphatic in nature, that is, they contain no more than one non-aliphatic moiety (cycloalkyl, cycloalkenyl or aromatic) group of 6 or less carbon atoms for every 10 carbon atoms in the substituent. Usually, however, the substituents contain no more than one such non-aliphatic group for every 50 carbon atoms, and in many cases, they contain no such non-aliphatic groups at all; that is, the typical substituents are purely aliphatic. Typically, these purely aliphatic substituents are alkyl or alkenyl groups.

Specific examples of the substantially saturated hydrocarbon- based substituents containing an average of more than 30 carbon atoms are the following:

a mixture of poly(ethylene/propylene) groups of about 35 to about 70 carbon atoms a mixture of the oxidatively or mechanically degraded poly(ethylene/propylene) groups of about 35 to about 70 carbon atoms a mixture of poly(propylene/1-hexene) groups of about 80 to about 150 carbon atoms a mixture of poly(isobutene) groups having an average of about 50 to about 200 carbon atoms A useful source of the substituents are poly(isobutene)s obtained by polymerization of a $C_4$ refinery stream having a butene content of about 35 to about 75 weight percent and isobutene content of about 30 to about 60 weight percent in the presence of a Lewis acid catalyst such as aluminum trichloride or boron trifluoride. These polybutenes contain predominantly (greater than 80% of total repeating units) isobutene repeating units of the configuration

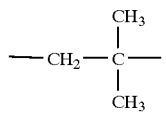

In one embodiment, the carboxylic acid acylating agent is a hydrocarbon substituted succinic acid or anhydride. The substituted succinic acid or anhydride consists of hydrocarbon-based substituent groups and succinic groups wherein the substituent groups are derived from a polyalkene, said acid or anhydride being characterized by the presence within its structure of an average of at least about 0.9 succinic group for each equivalent weight of substituent groups, and in one embodiment about 0.9 to about 2.5 succinic groups for each equivalent weight of substituent groups. The polyalkene generally has an ($\overline{Mn}$) of at least about 700, and in one embodiment about 700 to about 2000, and in one embodiment about 900 to about 1800. The ratio between the weight average molecular weight ($\overline{Mw}$) and the ($\overline{Mn}$) (that is, the $\overline{Mw}/\overline{Mn}$) can range from about 1 to about 10, or about 1.5 to about 5. In one embodiment the polyalkene has an $\overline{Mw}/\overline{Mn}$ value of about 2.5 to about 5. For purposes of this invention, the number of equivalent weights of substituent groups is deemed to be the number corresponding to the quotient obtained by dividing the $\overline{Mn}$ value of the polyalkene from which the substituent is derived into the total weight of the substituent groups present in the substituted succinic acid. Thus, if a substituted succinic acid is characterized by a total weight of substituent group of 40,000 and the $\overline{Mn}$ value for the polyalkene from which the substituent groups are derived is 2000, then that substituted succinic acylating agent is characterized by a total of 20 (40,000/2000=20) equivalent weights of substituent groups.

In one embodiment the carboxylic acid acylating agent is a substituted succinic acid or anhydride, said substituted succinic acid or anhydride consisting of hydrocarbon-based substituent groups and succinic groups wherein the substituent groups are derived from polybutene in which at least about 50% of the total units derived from butenes is derived from isobutylene. The polybutene is characterized by an $\overline{Mn}$ value of about 1500 to about 2000 and an $\overline{Mw}/\overline{Mn}$ value of about 3 to about 4. These acids or anhydrides are characterized by the presence within their structure of an average of about 1.5 to about 2.5 succinic groups for each equivalent weight of substituent groups.

In one embodiment the carboxylic acid is at least one substituted succinic acid or anhydride, said substituted succinic acid or anhydride consisting of substituent groups and succinic groups wherein the substituent groups are derived from polybutene in which at least about 50% of the total units derived from butenes is derived from isobutylene. The polybutene has an $\overline{Mn}$ value of about 800 to about 1200 and an $\overline{Mw}/\overline{Mn}$ value of about 2 to about 3. The acids or anhydrides are characterized by the presence within their structure of an average of about 0.9 to about 1.2 succinic groups for each equivalent weight of substituent groups.

The amino compound is characterized by the presence within its structure of at least one HN< group and can be a monoamine or polyamine. Mixtures of two or more amino compounds can be used in the reaction with one or more acylating reagents. In one embodiment, the amino compound contains at least one primary amino group (i.e., —$NH_2$) and more preferably the amine is a polyamine, especially a polyamine containing at least two —NH— groups, either or both of which are primary or secondary amines. The amines may be aliphatic, cycloaliphatic, aromatic or heterocyclic amines.

Among the useful amines are the alkylene polyamines, including the polyalkylene polyamines. The alkylene polyamines include those conforming to the formula

wherein n is from 1 to about 10; each R is independently a hydrogen atom, a hydrocarbyl group or a hydroxy-substituted or amine-substituted hydrocarbyl group having up to about 30 atoms, or two R groups on different nitrogen atoms can be joined together to form a U group, with the proviso that at least one R group is a hydrogen atom and U is an alkylene group of about 2 to about 10 carbon atoms. Preferably, U is ethylene or propylene. Especially preferred are the alkylene polyamines where each R is hydrogen or an amino-substituted hydrocarbyl group with the ethylene polyamines and mixtures of ethylene polyamines being the most preferred. Usually n will have an average value of from about 2 to about 7. Such alkylene polyamines include methylene polyamine, ethylene polyamines, propylene polyamines, butylene polyamines, pentylene polyamines, hexylene polyamines, heptylene polyamines, etc. The higher homologs of such amines and related amino alkyl-substituted piperazines are also included.

Alkylene polyamines that are useful include ethylene diamine, triethylene tetramine, propylene diamine, trimethylene diamine, hexamethylene diamine, decamethylene diamine, octamethylene diamine, di(heptamethylene) triamine, tripropylene tetramine, tetraethylene pentamine, trimethylene diamine, pentaethylene hexamine, di(trimethylene)triamine, N-(2-aminoethyl)piperazine, 1,4-bis(2-aminoethyl) piperazine, and the like. Higher homologs as are obtained by condensing two or more of the above-illustrated alkylene amines are useful, as are mixtures of two or more of any of the afore-described polyamines.

Ethylene polyamines, such as those mentioned above, are especially useful for reasons of cost and effectiveness. Such polyamines are described in detail under the heading "Diamines and Higher Amines" in The Encyclopedia of Chemical Technology, Second Edition, Kirk and Othmer, Volume 7, pages 27–39, Interscience Publishers, Division of John Wiley and Sons, 1965, which is hereby incorporated by reference for the disclosure of useful polyamines. Such compounds are prepared most conveniently by the reaction of an alkylene chloride with ammonia or by reaction of an ethylene imine with a ring-opening reagent such as ammonia, etc. These reactions result in the production of the somewhat complex mixtures of alkylene polyamines, including cyclic condensation products such as piperazines. These mixtures can be used.

Other useful types of polyamine mixtures are those resulting from stripping of the above-described polyamine mixtures. In this instance, lower molecular weight polyamines and volatile contaminants are removed from an alkylene polyamine mixture to leave as residue what is often termed "polyamine bottoms". In general, alkylene polyamine bottoms can be characterized as having less than two, usually less than 1% (by weight) material boiling below about 200° C. In the instance of ethylene polyamine bottoms, which are readily available and found to be quite useful, the bottoms contain less than about 2% (by weight) total diethylene triamine (DETA) or triethylene tetramine (TETA). A typical sample of such ethylene polyamine bottoms obtained from the Dow Chemical Company of Freeport, Tex. designated "E-100" showed a specific gravity at 15.6° C. of 1.0168, a percent nitrogen by weight of 33.15 and a viscosity at 40° C. of 121 centistokes. Gas chromatography analysis of such a sample showed it to contain about 0.93% "Light Ends" (most probably DETA), 0.72% TETA, 21.74% tetraethylene pentamine and 76.61 % pentaethylene hexamine and higher (by weight). These alkylene polyamine bottoms include cyclic condensation products such as piperazine and higher analogs of diethylenetriamine, triethylenetetramine and the like.

These alkylene polyamine bottoms can be reacted solely with the acylating agent, in which case the amino reactant consists essentially of alkylene polyamine bottoms, or they can be used with other amines and polyamines, or alcohols or mixtures thereof. In these latter cases at least one amino reactant comprises alkylene polyamine bottoms.

Other polyamines are described in, for example, U.S. Pat. Nos. 3,219,666 and 4,234,435, and these patents are hereby incorporated by reference for their disclosures of amines which can be reacted with the acylating agents described above to form the acylated nitrogen-containing compounds (B) of this invention.

In one embodiment, the amine may be a hydroxyamine. Typically, the hydroxyamines are primary, secondary or tertiary alkanol amines or mixtures thereof. Such amines can be represented by the formulae:

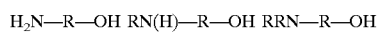

wherein each R is independently a hydrocarbyl group of one to about eight carbon atoms or hydroxyhydrocarbyl group of two to about eight carbon atoms, preferably one to about four, and R is a divalent hydrocarbyl group of about two to about 18 carbon atoms, preferably two to about four. The group —R —OH in such formulae represents the hydroxyhydrocarbyl group. R can be an acyclic, alicyclic or aromatic group. Typically, R is an acyclic straight or branched alkylene group such as an ethylene, 1,2-propylene, 1,2-butylene, 1,2-octadecylene, etc. group. Where two R groups are present in the same molecule they can be joined by a direct carbon-to-carbon bond or through a heteroatom (e.g., oxygen, nitrogen or sulfur) to form a 5-, 6-, 7- or 8-membered ring structure. Examples of such heterocyclic amines include N-(hydroxyl lower alkyl)-morpholines, -thiomorpholines, -piperidines, -oxazolidines, -thiazolidines and the like. Typically, however, each $R_1$ is independently a methyl, ethyl, propyl, butyl, pentyl or hexyl group.

Examples of these alkanolamines include mono-, di-, and triethanol amine, diethylethanolamine, ethylethanolamine, butyldiethanolamine, etc.

The hydroxyamines can also be an ether N-(hydroxyhydrocarbyl)-amine. These are hydroxypoly (hydrocarbyloxy) analogs of the above-described hydroxy amines (these analogs also include hydroxyl-substituted oxyalkylene analogs). Such N-(hydroxyhydrocarbyl) amines can be conveniently prepared by reaction of epoxides with afore-described amines and can be represented by the formulae:

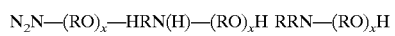

wherein x is a number from about 2 to about 15 and R and R are as described above. R may also be a hydroxypoly (hydrocarbyloxy) group.

The acylated nitrogen-containing compounds (B) include amine salts, amides, imides, amidines, amidic acids, amidic salts and imidazolines as well as mixtures thereof. To prepare the acylated nitrogen-containing compounds from the acylating reagents and the amino compounds, one or more acylating reagents and one or more amino compounds are heated, optionally in the presence of a normally liquid, substantially inert organic liquid solvent diluent, at temperatures in the range of about 80° C. up to the decomposition point of either the reactants or the carboxylic derivative but normally at temperatures in the range of about 100° C. up to about 300° C. provided 300° C. does not exceed the decomposition point. Temperatures of about 125° C. to about 250° C. are normally used. The acylating reagent and the amino compound are reacted in amounts sufficient to provide from about one-half equivalent up to about 2 moles of amino compound per equivalent of acylating reagent.

Many patents have described useful acylated nitrogen-containing compounds including U.S. Pat. Nos. 3,172,892; 3,219,666; 3,272,746; 3,310,492; 3,341,542; 3,444,170; 3,455,831; 3,455,832; 3,576,743; 3,630,904; 3,632,511; 3,804,763; and 4,234,435. A typical acylated nitrogen-containing compound of this class is that made by reacting a poly(isobutene)-substituted succinic acid acylating agent (e.g., anhydride, acid, ester, etc.) wherein the poly(isobutene) substituent has between about 50 to about 400 carbon atoms with a mixture of ethylenepolyamines having about 3 to about 7 amino nitrogen atoms per ethylenepolyamine and about 1 to about 6 ethylene units made from condensation of ammonia with ethylene chloride. The above-noted U.S. patents are hereby incorporated by reference for their disclosure of acylated amino compounds and their method of preparation.

Another type of acylated nitrogen compound belonging to this class is that made by reacting a carboxylic acid acylating agent with a polyamine, wherein the polyamine is the product made by condensing a hydroxy material with an amine. These compounds are described in U.S. Pat. No. 5,053,152 which is incorporated herein by reference for its disclosure of such compounds.

Another type of acylated nitrogen compound belonging to this class is that made by reacting the afore described alkyleneimines with the afore-described substituted succinic acids or anhydrides and aliphatic monocarboxylic acids having from 2 to about 22 carbon atoms. In these types of acylated nitrogen compounds, the mole ratio of succinic acid to monocarboxylic acid ranges from about 1:0.1 to about 1:1. Typical of the monocarboxylic acid are formic acid, acetic acid, dodecanoic acid, butanoic acid, oleic acid, stearic acid, the commercial mixture of stearic acid isomers known as isostearic acid, tall oil acid, etc. Such materials are more fully described in U.S. Pat. Nos. 3,216,936 and 3,250,715 which are hereby incorporated by reference for their disclosures in this regard.

Still another type of acylated nitrogen compound useful in making the compositions of this invention is the product of the reaction of a fatty monocarboxylic acid of about 12–30 carbon atoms and the afore-described alkyleneamines, typically, ethylene-, propylene- or trimethylenepolyamines containing 2 to 8 amino groups and mixtures thereof. The fatty monocarboxylic acids are generally mixtures of straight and branched chain fatty carboxylic acids containing 12–30 carbon atoms. A widely used type of acylated nitrogen compound is made by reacting the afore-described alkylenepolyamines with a mixture of fatty acids having from 5 to about 30 mole percent straight chain acid and about 70 to about 95% mole branched chain fatty acids. Among the commercially available mixtures are those known widely in the trade as isostearic acid. These mixtures are produced as a by-product from the dimerization of unsaturated fatty acids as described in U.S. Pat. Nos. 2,812,342 and 3,260,671.

The branched chain fatty acids can also include those in which the branch is not alkyl in nature, such as found in phenyl and cyclohexyl stearic acid and the chloro-stearic acids. Branched chain fatty carboxylic acid/alkylene polyamine products have been described extensively in the art. See for example, U.S. Pat. Nos. 3,110,673; 3,251,853; 3,326,801; 3,337,459; 3,405,064; 3,429,674; 3,468,639; 3,857,791. These patents are hereby incorporated by reference for their disclosure of fatty acid/polyamine condensates for use in lubricating oil formulations.

The following specific examples illustrate the preparation of exemplary acylated nitrogen-containing compounds (B) useful with this invention.

EXAMPLE B-1

1000 parts by weight of polyisobutylene ($\overline{M}n$=1700) substituted succinic anhydride and 1270 parts by weight of diluent oil are blended together and heated to 110° C. 59.7 parts by weight of a mixture of polyethyleneamine bottoms and diethylenetriamine are added over a two-hour period. The mixture exotherms to 121–132° C. The mixture is heated to 149° C. with nitrogen blowing. The mixture is maintained at 149–154° C. for one hour with nitrogen blowing. The mixture is then filtered at 149° C. Diluent oil is added to provide a mixture having an oil content of 55% by weight.

EXAMPLE B-2

A blend of 800 parts by weight of polyisobutylene ($\overline{M}n$=940) substituted succinic anhydride and 200 parts by weight of diluent oil is heated to 150° C. with a nitrogen sparge. 87.2 parts by weight of methylpentaerythritol are added over a one-hour period while maintaining the temperature at 150–160° C. The mixture is heated to 204° C. over a period of eight hours, and maintained at 204–210° C. for six hours. 15.2 parts by weight of a mixture of polyethyleneamine bottoms and diethylenetriamine are added over a one-hour period while maintaining the temperature of the mixture at 204–210° C. 519.5 parts of diluent oil are added to the mixture while maintaining the temperature at a minimum of 177° C. The mixture is cooled to 130° C. and filtered to provide the desired product.

(C) Phosphorus Compound.

The phosphorus compound (C) can be a phosphorus acid, ester or derivative thereof. These include phosphorus acid, phosphorus acid ester, phosphorus acid salt, or derivative thereof. The phosphorus acids include the phosphoric, phosphonic, phosphinic and thiophosphoric acids including dithiophosphoric acid as well as the monothiophosphoric, thiophosphinic and thiophosphonic acids.

The phosphorus compound (C) can be a phosphorus acid ester derived from a phosphorus acid or anhydride and an alcohol of 1 to about 50 carbon atoms, and in one embodiment 1 to about 30 carbon atoms. It can be a phosphite, a monothiophosphate, a dithiophosphate, or a dithiophosphate disulfide. It can also be a metal, amine or ammonium salt of a phosphorus acid or phosphorus acid ester. It can be a phosphorus containing amide or a phosphorus-containing carboxylic ester.

The phosphorus compound can be a phosphate, phosphonate, phosphinate or phosphine oxide. These compounds can be represented by the formula

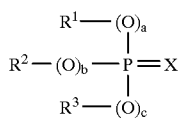

(C-I)

wherein in Formula (C-I), $R^1$, $R^2$ and $R^3$ are independently hydrogen or hydrocarbyl groups, X is O or S, and a, b and c are independently zero or 1. The phosphorus compound can be a phosphite, phosphonite, phosphinite or phosphine. These compounds can be represented by the formula

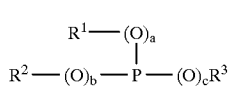

(C-II)

wherein in Formula (C-II), $R^1$, $R^2$ and $R^3$ are independently hydrogen or hydrocarbyl groups, and a, b and c are independently zero or 1.

The total number of carbon atoms in $R^1$, $R^2$ and $R^3$ in each of the above Formulae (C-I) and (C-II) must be sufficient to render the compound soluble in the low-viscosity oil used in formulating the inventive compositions. Generally, the total number of carbon atoms in $R^1$, $R^2$ and $R^3$ is at least about 8, and in one embodiment at least about 12, and in one embodiment at least about 16. There is no limit to the total number of carbon atoms in $R^1$, $R^2$ and $R^3$ that is required, but a practical upper limit is about 400 or about 500 carbon atoms. In one embodiment, $R^1$, $R^2$ and $R^3$ in each of the above formulae are independently hydrocarbyl groups of 1 to about 100 carbon atoms, or 1 to about 50 carbon atoms, or 1 to about 30 carbon atoms, with the proviso that the total number of carbons is at least about 8. Each $R^1$, $R^2$ and $R^3$ can be the same as the other, although they may be different. Examples of useful $R^1$, $R^2$ and $R^3$ groups include isopropyl, n-butyl, isobutyl, amyl, 4-methyl-2-pentyl, isooctyl, decyl, dodecyl, tetradecyl, 2-pentenyl, dodecenyl, phenyl, naphthyl, alkylphenyl, alkylnaphthyl, phenylalkyl, naphthylalkyl, alkylphenylalkyl, alkylnaphthylalkyl, and the like.

The phosphorus compounds represented by Formulae (C-I) and (C-II) can be prepared by reacting a phosphorus acid or anhydride with an alcohol or mixture of alcohols corresponding to $R^1$, $R^2$ and $R^3$ in Formulae (C-I) and (C-II). The phosphorus acid or anhydride is generally an inorganic phosphorus reagent such as phosphorus pentoxide, phosphorus trioxide, phosphorus tetraoxide, phosphorus acid, phosphorus halide, or lower phosphorus esters, and the like. Lower phosphorus acid esters contain from 1 to about 7 carbon atoms in each ester group. The phosphorus acid ester may be a mono-, di- or triphosphoric acid ester.

The phosphorus compound (C) can be a compound represented by the formula

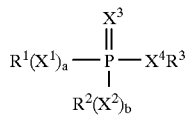

(C-III)

wherein in Formula (C-III): $X^1$, $X^2$, $X^3$ and $X^4$ are independently oxygen or sulfur, and $X_1$ and $X^2$ can be $NR^4$; a and b are independently zero or one; $R^1$, $R^2$ $R^3$ and $R^4$ are independently hydrocarbyl groups, and $R^3$ and $R^4$ can be hydrogen.

Useful phosphorus compounds of the type represented by Formula (C-III) are phosphorus- and sulfur-containing compounds. These include those compounds wherein at least one $X^3$ or $X^4$ is sulfur, and in one embodiment both $X^3$ and $X^4$ are sulfur, at least one $X_1$ or $X^2$ is oxygen or sulfur, and in one embodiment both $X_1$ and $X^2$ are oxygen, a and b are each 1, and $R^3$ is hydrogen. Mixtures of these compounds may be employed in accordance with this invention.

In Formula (C-III), $R^1$ and $R^2$ are independently hydrocarbyl groups that are preferably free from acetylenic unsaturation and usually also from ethylenic unsaturation and in one embodiment have from about 1 to about 50 carbon atoms, and in one embodiment from about 1 to about 30 carbon atoms, and in one embodiment from about 1 to about 18 carbon atoms, and in one embodiment from about 1 to about 8 carbon atoms. Each $R^1$ and $R^2$ can be the same as the other, although they may be different and either or both may be mixtures. Examples of $R^1$ and $R^2$ groups include isopropyl, n-butyl, isobutyl, amyl, 4-methyl-2-pentyl, isooctyl, decyl, dodecyl, tetradecyl, 2-pentenyl, dodecenyl, phenyl, naphthyl, alkylphenyl, alkylnaphthyl, phenylalkyl, naphthylalkyl, alkylphenylalkyl, alkylnaphth-lkyl, and mixtures thereof. Particular examples of useful mixtures include, for example, isopropyl/n-butyl; isopropyl/secondary butyl; isopropyl/4-methyl-2-pentyl; isopropyl/2-ethyl-1-hexyl; isopropyl/isooctyl; isopropyl/decyl; isopropyl/dodecyl; and isopropyl tridecyl.

In Formula (C-III), $R^3$ and $R^4$ are independently hydrogen or hydrocarbyl groups (e.g. alkyl) of 1 to about 12 carbon atoms, and in one embodiment 1 to about 4 carbon atoms. $R^3$ is preferably hydrogen.

Phosphorus compounds corresponding to Formula (C-III) wherein $X^3$ and $X^4$ are sulfur can be obtained by the reaction of phosphorus pentasulfide ($P_2S_5$) and an alcohol or mixture of alcohols corresponding to $R^1$ and $R^2$. The reaction involves mixing at a temperature of about 20° C. to about 200° C., four moles of alcohol with one mole of phosphorus pentasulfide. Hydrogen sulfide is liberated in this reaction. The oxygen-containing analogs of these compounds can be prepared by treating the dithioic acid with water or steam which, in effect, replaces one or both of the sulfur atoms.

In one embodiment, the phosphorus compound (C) is a monothiophosphoric acid ester or a monothiophosphate. Monothiophosphates are prepared by the reaction of a sulfur source and a dihydrocarbyl phosphite. The sulfur source may be elemental sulfur, a sulfide, such as a sulfur coupled olefin or a sulfur coupled dithiophosphate. Elemental sulfur is a useful sulfur source. The preparation of monothiophosphates is disclosed in U.S. Pat. No. 4,755,311 and PCT Publication WO 87/07638 which are incorporated herein by reference for their disclosure of monothiophosphates, sulfur sources for preparing monothiophosphates and the process for making monothiophosphates.

Monothiophosphates may also be formed in the lubricant blend or functional fluid by adding a dihydrocarbyl phosphite to a lubricating oil composition or functional fluid containing a sulfur source. The phosphite may react with the sulfur source under blending conditions (i.e., temperatures from about 30° C. to about 100° C. or higher) to form the monothiophosphate.

Useful phosphorus acid esters include those prepared by reacting a phosphoric acid or anhydride with cresol alcohols. An example is tricresol phosphate.

In one embodiment, the phosphorus compound (C) is a dithiophosphoric acid or phosphorodithioic acid. The dithiophosphoric acid can be reacted with an epoxide or a glycol to form an intermediate. The intermediate is then reacted with a phosphorus acid, anhydride, or lower ester. The epoxide is generally an aliphatic epoxide or a styrene oxide. Examples of useful epoxides include ethylene oxide, propylene oxide, butene oxide, octene oxide, dodecene oxide, styrene oxide, etc. Propylene oxide is useful. The glycols may be aliphatic glycols having from 1 to about 12, and in one embodiment about 2 to about 6, and in one embodiment 2 or 3 carbon atoms, or aromatic glycols. Aliphatic glycols include ethylene glycol, propylene glycol, triethylene glycol and the like. Aromatic glycols include hydroquinone, catechol, resorcinol, and the like. These are described in U.S. Pat. No. 3,197,405 which is incorporated herein by reference for its disclosure of dithiophosphoric acids, glycols, epoxides, inorganic phosphorus reagents and methods of reacting the same.

In one embodiment the phosphorus compound (C) is a phosphite. The phosphite can be a di- or trihydrocarbyl phosphite. Each hydrocarbyl group can have from 1 to about 24 carbon atoms, or from 1 to about 18 carbon atoms, or from about 2 to about 8 carbon atoms. Each hydrocarbyl group may be independently alkyl, alkenyl or aryl. When the hydrocarbyl group is an aryl group, then it contains at least about 6 carbon atoms; and in one embodiment about 6 to about 18 carbon atoms. Examples of the alkyl or alkenyl groups include propyl, butyl, hexyl, heptyl, octyl, oleyl, linoleyl, stearyl, etc. Examples of aryl groups include phenyl, naphthyl, heptylphenol, etc. In one embodiment each hydrocarbyl group is independently propyl, butyl, pentyl, hexyl, heptyl, oleyl or phenyl, more preferably butyl, oleyl or phenyl and more preferably butyl or oleyl. Phosphites and their preparation are known and many phosphites are available commercially. Useful phosphites include dibutyl hydrogen phosphite, trioleyl phosphite and triphenyl phosphite.

In one embodiment, the phosphorus compound (C) is a phosphorus-containing amide. The phosphorus-containing amides may be prepared by the reaction of a phosphorus acid (e.g., a dithiophosphoric acid as described above) with an unsaturated amide. Examples of unsaturated amides include acrylamide, N,N-methylenebisacrylamide, methacrylamide, crotonamide, and the like. The reaction product of the phosphorus acid with the unsaturated amide may be further reacted with linking or coupling compounds, such as formaldehyde or paraformaldehyde to form coupled compounds. The phosphorus-containing amides are known in the art and are disclosed in U.S. Pat. Nos. 4,876,374, 4,770,807 and 4,670,169 which are incorporated by reference for their disclosures of phosphorus amides and their preparation.

In one embodiment, the phosphorus compound (C) is a phosphorus-containing carboxylic ester. The phosphorus-containing carboxylic esters may be prepared by reaction of one of the above-described phosphorus acids, such as a dithiophosphoric acid, and an unsaturated carboxylic acid or ester, such as acrylic acid or a vinyl or allyl carboxylic acid or ester. If the carboxylic acid is used, the ester may then be formed by subsequent reaction with an alcohol.

The vinyl ester of a carboxylic acid may be represented by the formula RCH═CH—O(O)CR$^1$ wherein R is a hydrogen or hydrocarbyl group having from 1 to about 30 carbon atoms, preferably hydrogen or a hydrocarbyl group having 1 to about 12, more preferably hydrogen, and R$^1$ is a hydrocarbyl group having 1 to about 30 carbon atoms, preferably 1 to about 12, more preferably 1 to about 8. Examples of vinyl esters include vinyl acetate, vinyl 2-ethylhexanoate, vinyl butanoate, and vinyl crotonate.

In one embodiment, the unsaturated carboxylic ester is an ester of an unsaturated carboxylic acid, such as maleic, fumaric, acrylic, methacrylic, itaconic, citraconic acids and the like. The ester can be represented by the formula RO—(O)C—HC═CH—C(O)OR wherein each R is independently a hydrocarbyl group having 1 to about 18 carbon atoms, or 1 to about 12, or 1 to about 8 carbon atoms. Examples of unsaturated carboxylic esters that are useful include methylacrylate, ethylacrylate, 2-ethylhexylacrylate, 2-hydroxyethylacrylate, ethylmethacrylate, 2-hydroxyethylmethacrylate, 2-hydroxypropylmethacrylate, 2-hydroxypropylacrylate, ethylmaleate, butylmaleate and 2-ethylhexylmaleate. The above list includes mono- as well as diesters of maleic, fumaric and citraconic acids.

In one embodiment, the phosphorus compound (C) is the reaction product of a phosphorus acid and a vinyl ether. The vinyl ether is represented by the formula R—CH$_2$═CH—OR$^1$ wherein R is hydrogen or a hydrocarbyl group having 1 to about 30, preferably 1 to about 24, more preferably 1 to about 12 carbon atoms, and R$^1$ is a hydrocarbyl group having 1 to about 30 carbon atoms, preferably 1 to about 24, more preferably 1 to about 12 carbon atoms. Examples of vinyl ethers include vinyl methylether, vinyl propylether, vinyl 2-ethylhexylether and the like.

When the phosphorus compound (C) is acidic, it may be reacted with an ammonia or a source of ammonia, an amine, or metallic base to form the corresponding salt. The salts may be formed separately and then added to the lubricating oil or functional fluid composition. Alternatively, the salts may be formed when the acidic phosphorus compound (C) is blended with other components to form the lubricating oil or functional fluid composition. The phosphorus compound can then form salts with basic materials which are in the lubricating oil or functional fluid composition such as basic nitrogen containing compounds (e.g., the above-discussed acylated nitrogen-containing compounds (B)) and overbased materials.

The metal salts which are useful with this invention include those salts containing Group IA, IIA or IIB metals, aluminum, lead, tin, iron, molybdenum, manganese, cobalt, nickel or bismuth. Zinc is an especially useful metal. These salts can be neutral salts or basic salts. Examples of useful metal salts of phosphorus-containing acids, and methods for preparing such salts are found in the prior art such as U.S. Pat. Nos. 4,263,150, 4,289,635; 4,308,154; 4,322,479; 4,417,990; and 4,466,895, and the disclosures of these patents are hereby incorporated by reference. These salts include the Group II metal phosphorodithioates such as zinc dicyclohexylphosphorodithioate, zinc dioctylphosphorodithioate, barium di(heptylphenyl)-phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

The following examples illustrate the preparation of useful metal salts of the phosphorus compounds (C).

EXAMPLE C-1

(a) A mixture of 317.33 grams (5.28 moles) of 2-propanol and 359.67 grams (3.52 moles) of 4-methyl-2-pentanol is prepared and heated to 60° C. Phosphorus pentasulfide (444.54 grams, 2.0 moles) is added to the alcohol mixture while maintaining the temperature at 60° C. Two moles of hydrogen sulfide are liberated and trapped with a 50% aqueous sodium hydroxide trap. The mixture is heated to and maintained at 70° C. for two hours. The mixture is cooled to room temperature and filtered through diatomaceous earth to yield a liquid green product having an acid number in the range of 193–203.

(b) 89.1 grams (1.1 moles) of ZnO are added to 200 ml of toluene. 566.6 grams (2.0 equivalents based on acid number) of the product from part (a) are added dropwise to the ZnO/toluene mixture. The resulting reaction is exothermic. The reaction mixture is stripped to 70° C. and 20 mm Hg to remove water of reaction, toluene and excess alcohol. The residue is filtered through diatomaceous earth. The filtrate, which is the desired product, is a yellow viscous liquid.

EXAMPLE C-2

137.6 grams of zinc oxide are mixed with 149.9 grams of diluent oil. 17.7 grams of 2-ethylhexanoic acid are added. 1000 grams of a phosphorodithioic acid derived from $P_2S_5$ and 2-ethylhexanol are then added to the mixture. The mixture is allowed to neutralize. It is then flash dried and vacuum stripped. 81.1 grams of triphenyl phosphite are added. The temperature of the mixture is adjusted to 124–129° C. and maintained at that temperature for three hours. The mixture is cooled to room temperature and filtered using filter aid to provide the desired product.

When the phosphorus compound (C) is an ammonium salt, the salt is considered as being derived from ammonia ($NH_3$) or an ammonia yielding compound such as $NH_4OH$. Other ammonia yielding compounds will readily occur to those skilled in the art.

When the phosphorus compound (C) is an amine salt, the salt may be considered as being derived from amines. Any of the amines discussed above under the subtitle "(B) Acylated Nitrogen-Containing Compounds" can be used.

The following examples illustrate the preparation of amine or ammonium salts of the phosphorus compounds (C) that can be used with this invention.

EXAMPLE C-3

Phosphorus pentoxide (208 grams, 1.41 moles) is added at 50° C. to 60° C. to hydroxypropyl O,O'-diisobutylphosphorodithioate (prepared by reacting 280 grams of propylene oxide with 1184 grams of O,O'-diisobutylphosphorodithioic acid at 30° C. to 60° C.). The reaction mixture is heated to 80° C. and held at that temperature for 2 hours. To the acidic reaction mixture there is added a stoichiometrically equivalent amount (384 grams) of a commercial aliphatic primary amine at 30° C. to 60° C. The product is filtered. The filtrate has a phosphorus content of 9.31%, a sulfur content of 11.37%, a nitrogen content of 2.50%, and a base number of 6.9 (bromphenol blue indicator).

EXAMPLE C-4

(a) O,O-di-(2-ethylhexyl) dithiophosphoric acid (354 grams) having an acid number of 154 is introduced into a stainless steel "shaker" type autoclave of 1320 ml capacity having a thermostatically controlled heating jacket. Propylene oxide is admitted until the pressure rises to 170 psig at room temperature, and then the autoclave is sealed and shaken for 4 hours at 50° C. to 100° C. during which time the pressure rises to a maximum of 550 psig. The pressure decreases as the reaction proceeds. The autoclave is cooled to room temperature, the excess propylene oxide is vented and the contents removed. The product (358 grams), a dark liquid having an acid number of 13.4, is substantially O,O-di-(2-ethylhexyl)-S-hydroxyisopropyl dithiophosphate.

(b) Ammonia is blown into the product of part (a) until a substantially neutral product is obtained.

The phosphorus compound (C) can be a phosphorus-containing sulfide represented by the formula

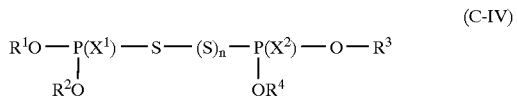
(C-IV)

wherein in Formula (C-IV), $R^1$, $R^2$, $R^3$ and $R^4$ are independently hydrocarbyl groups, $X^1$ and $X^2$ are independently O or S, and n is zero to 3. In one embodiment $X^1$ and $X^2$ are each S, and n is 1. $R^1$, $R^2$, $R^3$ and $R^4$ are independently hydrocarbyl groups that are preferably free from acetylenic unsaturation and usually also free from ethylenic unsaturation. In one embodiment $R^1$, $R^2$, $R^3$ and $R^4$ independently have from about 1 to about 50 carbon atoms, and in one embodiment from about 1 to about 30 carbon atoms, and in one embodiment from about 1 to about 18 carbon atoms, and in one embodiment from about 1 to about 8 carbon atoms. Each $R^1$, $R^2$, $R^3$ and $R^4$ can be the same as the other, although they may be different and mixtures may be used. Examples of $R^1$, $R^2$, $R^3$ and $R^4$ groups include isopropyl, butyl, n-butyl, isobutyl, amyl, 4-methyl-2-pentyl, octyl, isooctyl, decyl, dodecyl, tetradecyl, 2-pentenyl, dodecenyl, phenyl, naphthyl, alkylphenyl, alkylnaphthyl, phenylalkyl, naphthylalkyl, alkylphenylalkyl, alkylnaphthylalkyl, and mixtures thereof.

The compounds represented by Formula (C-IV) can be prepared by first reacting an alcohol, phenol or aliphatic or aromatic mercaptan with a sulfide of phosphorus, such as $P_2S_3$, $P_2S_5$, $P_4S_3$, $P_4S_7$, $P_4S_{10}$, and the like, to form a partially esterified thiophosphorus or thiophosphoric acid, and then further reacting this product as such or in the form of a metal salt with an oxidizing agent or with a sulfur halide. Thus, when an alcohol is reacted with phosphorus trisulfide, a dialkylated monothiophosphorus acid is formed according to the following equation:

$$4ROH + P_2S_3 \rightarrow 2(RO)_2PSH + H_2S$$

This alkylated thiophosphorus acid may then be treated with an oxidizing agent such as hydrogen peroxide or with sulfur dichloride or sulfur monochloride to form a disulfide, trisulfide, or tetrasulfide, respectively, according to the following equations:

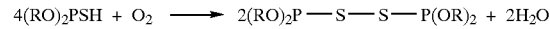

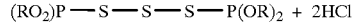

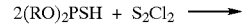
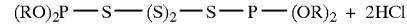

Similarly, when the alcohol is reacted with phosphorus pentasulfide, the corresponding di-substituted dithiophosphoric acid is formed, and this may likewise be converted into disulfide, trisulfide or tetrasulfide compounds. Suitable alcohols such as those discussed below may be employed. Sulfurized alcohols such as sulfurized oleyl alcohol may also be used. Corresponding reactions take place by starting with mercaptans, phenols or thiophenols instead of alcohols. Suitable oxidizing agents for converting the thiophosphorus and thiophosphoric acids to disulfides include iodine, potassium triodide, ferric chloride, sodium hypochlorite, hydrogen peroxide, oxygen, etc.

Alcohols used to prepare the phosphorus-containing sulfides of Formula (C-IV) can be any of the alcohols described above under the subtitle "(A) Mixed Polysulfides."

The following examples illustrate the preparation of phosphorus-containing sulfides (C) represented by Formula (C-IV) that are useful with this invention.

EXAMPLE C-5

A phosphorodithioic acid derived from $P_2S_5$ and an alcohol mixture of 40% by weight isopropyl alcohol and 60% by weight 4-methyl-secondary-amyl alcohol (4518 grams, 14.34 equivalents) is charged to a reactor. A 30% aqueous hydrogen peroxide solution (1130 grams, 10.0 moles) is added dropwise at a rate of 7.3 grams per minute. The temperature of the reaction mixture increases from 24° C. to 38° C. A 50% aqueous sodium hydroxide solution (40 grams, 0.50 equivalents) is added. The reaction mixture is stirred for 5 minutes, and then allowed to stand. The mixture separates into two layers. The aqueous layer contains water, phosphorodithioic acid salt and excess alcohol from the phosphorodithioic acid. The organic layer contains the desired product. The aqueous layer is drawn off (1108 grams) and the remaining organic portion is stripped at 100° C. and 20 mm Hg for two hours. The stripped organic product is filtered using a filter aid to provide the desired product which is a phosphorus-containing disulfide in the form of a clear yellow liquid (4060 grams).

EXAMPLE C-6

A phosphorodithioic acid derived from 4-methyl-2-pentanol and $P_2S_5$ (1202 grams, 3.29 equivalents) is charged to a reactor. A 30% aqueous hydrogen peroxide solution (319 grams, 2.82 moles) is added dropwise at a rate of 7.3 grams per minute. The temperature of the reaction mixture increases from 24° C. to 38° C. A 50% aqueous sodium hydroxide solution (12 grams, 0.15 equivalents) is added. The reaction mixture is stirred for 5 minutes, and then allowed to stand. The mixture separates into two layers. The aqueous layer contains water, phosphorodithioic acid salt and excess methylamyl alcohol from the phosphorodithioic acid. The organic layer contains the desired product. The aqueous layer is drawn off and the remaining organic portion is stripped at 100° C. and 20 mm Hg for two hours. The stripped organic product is filtered using filter aid to provide the desired phosphorus-containing disulfide product which is a clear yellow liquid (1016 grams).

EXAMPLE C-7

(a) A mixture of 105.6 grams (1.76 moles) of isopropyl alcohol and 269.3 grams (2.64 moles) of 4-methyl-2-pentanol is prepared and heated to 70° C. Phosphorus pentasulfide (222 grams, 1 mole) is added to the alcohol mixture while maintaining the temperature at 70° C. One mole of hydrogen sulfide is liberated. The mixture is maintained at 70° C. for an additional four hours. The mixture is filtered through diatomaceous earth to yield a green liquid product having an acid number in the range of 179–189.

(b) 44.6 grams (1.09 equivalents) of ZnO are added to diluent oil to form a slurry. One equivalent (based upon the measured acid number) of the phosphorodithioic acid prepared in (a) are added dropwise to the ZnO slurry. The reaction is exothermic. The reaction mixture is stripped to 100° C. and 20 mm Hg to remove water of reaction and excess alcohol. The residue is filtered through diatomaceous earth. The filtrate, which is a viscous liquid, is diluted with diluent oil to provide a final product having a 9.5% by weight phosphorus content.

(c) A mixture of the product of part (a) of this example (184 grams) and part (b) (130 grams) is placed in a reactor. A 30% aqueous hydrogen peroxide solution (80 grams) is added dropwise. After the hydrogen peroxide addition is complete, the reaction mixture is stripped at 70° C. and 20 mm Hg. The reaction mixture is filtered through diatomaceous earth to provide the desired product which is in the form of a yellow liquid.

(D) Thiocarbamate.

Component (D) is a thiocarbamate which can be represented by the formula

$$R^1R^2N-C(X)S-(CR^3R^4)_aZ \qquad (D\text{-}I)$$

wherein in Formula (D-I), $R^1$, $R^2$, $R^3$ and $R^4$ are independently hydrogen or hydrocarbyl groups, provided that at least one of $R^1$ or $R^2$ is a hydrocarbyl group; X is O or S; a is 1 or 2; and Z is a hydrocarbyl group, a hetero group (that is, a group attached through a hetero atom such as O, N, or S), a hydroxy hydrocarbyl group, an activating group, or a group represented by the formula —(S)C(X)—$NR^1R^2$.

When a is 2, Z is an activating group. In describing Z as an "activating group," what is meant is a group which will activate an olefin to which it is attached toward nucleophilic addition by, e.g., $CS_2$ or COS derived intermediates. (This is reflective of a method by which this material can be prepared, by reaction of an activated olefin with $CS_2$ and an amine.) The activating group Z can be, for instance, an ester group, typically but not necessarily a carboxylic ester group of the structure —$COOR^5$. It can also be an ester group based on a non-carbon acid, such as a sulfonic or sulfinic ester or a phosphonic or phosphinic ester. The activating group can also be any of the acids corresponding to the aforementioned esters. Z can also be an amide group, that is, based on the condensation of an acid group, preferably a carboxylic acid group, with an amine. In that case the —$(CR^3R^4)_aZ$ group can be derived from acrylamide. Z can also be an ether group, —$OR^5$; a carbonyl group, that is, an aldehyde or a ketone group; a cyano group, —CN, or an aryl group. In one embodiment Z is an ester group of the structure, —$COOR^5$, where $R^5$ is a hydrocarbyl group. $R^5$ can comprise 1 to about 18 carbon atoms, and in one embodiment 1 to about 6 carbon atoms. In one embodiment $R^5$ is methyl so that the activating group is —$COOCH_3$.

When a is 1, Z need not be an activating group, because the molecule is generally prepared by methods, described below, which do not involve nucleophilic addition to an activated double bond.

When Z is a hydrocarbyl or a hydroxy hydrocarbyl group, a can be zero, 1 or 2. These hydrocarbyl groups can have from 1 to about 30 carbon atoms, and in one embodiment 1 to about 18 carbon atoms, and in one embodiment 1 to about 12 carbon atoms. Examples include methyl, ethyl, propyl, n-butyl, isobutyl, pentyl, isopentyl, heptyl, octyl, 2-ethylhexyl, nonyl, decyl, dodecyl, and the corresponding hydroxy-substituted hydrocarbyl groups such as hydroxymethyl, hydroxyethyl, hydroxypropyl, etc.

$R^3$ and $R^4$ can be, independently, hydrogen or methyl or ethyl groups. When a is 2, at least one of $R^3$ and $R^4$ is normally hydrogen so that this compound will be $R^1R^2N$—C(S)S—$CR^3HCR^3R^4COOR^5$. In one embodiment the thiocarbamate is $R^1R^2N$—C(S)S—$CH_2CH_2COOCH_3$. (These materials can be derived from methyl methacrylate and methyl acrylate, respectively.) These and other materials containing appropriate activating groups are disclosed in greater detail in U.S. Pat. No. 4,758,362, which is incorporated herein by reference.

The substituents $R^1$ and $R^2$ on the nitrogen atom are likewise hydrogen or hydrocarbyl groups, but at least one should be a hydrocarbyl group. It is generally believed that at least one such hydrocarbyl group is desired in order to provide a measure of oil-solubility to the molecule. However, $R^1$ and $R^2$ can both be hydrogen, provided the other R groups in the molecule provide sufficient oil solubility to the molecule. In practice this means that at least one of the groups $R^3$ or $R^4$ should be a hydrocarbyl group of at least 4 carbon atoms. In one embodiment, $R^1$ and $R^2$ can be independently hydrocarbyl groups (e.g., aliphatic hydrocarbyl groups such as alkyl groups) of 1 to about 50 carbon atoms, and in one embodiment 1 to about 30 carbon atoms, and in one embodiment 1 to about 18 carbon atoms, and in one embodiment 1 to about 12 carbon atoms, and in one embodiment 1 to about 8 carbon atoms.

In one embodiment the thiocarbamate is a compound represented by the formula

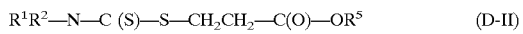
$$R^1R^2\text{—}N\text{—}C\,(S)\text{—}S\text{—}CH_2CH_2\text{—}C(O)\text{—}OR^5 \qquad (D\text{-}II)$$

wherein in Formula (D-II) $R^1$, $R^2$ and $R^5$ are independently hydrocarbyl (e.g., alkyl) groups. These hydrocarbyl groups can have from 1 to about 18 carbon atoms, and in one embodiment 1 to about 12 carbon atoms, and in one embodiment 1 to about 8 carbon atoms, and in one embodiment 1 to about 4 carbon atoms. These compounds include S-carbomethoxyethyl-N,N-dibutyl dithiocarbamate which can be represented by the formula

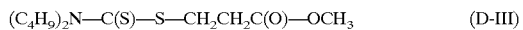
$$(C_4H_9)_2N\text{—}C(S)\text{—}S\text{—}CH_2CH_2C(O)\text{—}OCH_3 \qquad (D\text{-}III)$$

Materials of this type can be prepared by a process described in U.S. Pat. No. 4,758,362. Briefly, these materials are prepared by reacting an amine, carbon disulfide or carbonyl sulfide, or source materials for these reactants, and a reactant containing an activated, ethylenically-unsaturated bond or derivatives thereof. These reactants are charged to a reactor and stirred, generally without heating, since the reaction is normally exothermic. Once the reaction reaches the temperature of the exotherm (typically 40–65° C.), the reaction mixture is held at the temperature to insure complete reaction. After a reaction time of typically 3–5 hours, the volatile materials are removed under reduced pressure and the residue is filtered to yield the final product.

The relative amounts of the reactants used to prepare these compounds are not critical. The charge ratios to the reactor can vary where economics and the amount of the product desired are controlling factors. Thus, the molar charge ratio of the amine to the $CS_2$ or COS reactant to the ethylenically unsaturated reactant may vary in the ranges 5:1:1 to 1:5:1 to 1:1:5. In one embodiment, the charge ratios of these reactants is 1:1:1.

In the case where a is 1, the activating group Z is separated from the sulfur atom by a methylene group. Materials of this type can be prepared by reaction of sodium dithiocarbamate with a chlorine-substituted material. Such materials are described in greater detail in U.S. Pat. No. 2,897,152, which is incorporated herein by reference.

The following example illustrates the preparation of a thiocarbamate (D) that can be used with this invention.

EXAMPLE D-1

Carbon disulfide (79.8 grams, 1.05 moles) and methyl acrylate (86 grams, 1.0 mole) are placed in a reactor and stirred at room temperature. Di-n-butylamine (129 grams, 1.0 mole) is added dropwise to the mixture. The resulting reaction is exothermic, and the di-n-butylamine addition is done at a sufficient rate to maintain the temperature at 55° C. After the addition of di-n-butylamine is complete, the reaction mixture is maintained at 55° C. for four hours. The mixture is blown with nitrogen at 85° C. for one hour to remove unreacted starting material. The reaction mixture is filtered through filter paper, and the resulting product is a viscous orange liquid.

(E) Organic Sulfide.

The organic sulfides (E) that are useful with this invention are compounds represented by the formula

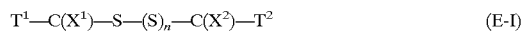
$$T^1\text{—}C(X^1)\text{—}S\text{—}(S)_n\text{—}C(X^2)\text{—}T^2 \qquad (E\text{-}I)$$

wherein in Formula (E-I), $T^1$ and $T^2$ are independently R, OR, SR or NRR wherein each R is independently a hydrocarbyl group, $X_1$ and $X^2$ are independently O or S, and n is zero to 3. In one embodiment, $X^1$ and $X^2$ are each S. In one embodiment, n is 1 to 3, and in one embodiment, n is 1. Thus, compounds represented by the formula

$$T^1\text{—}C(S)\text{—}S\text{—}S\text{—}C(S)\text{—}T^2 \qquad (E\text{-}II)$$

wherein in Formula (E-II), $T^1$ and $T^2$ are as defined above can be used. In one embodiment, each R is a hydrocarbyl group of 1 to about 50 carbon atoms, and in one embodiment 1 to about 40 carbon atoms, and in one embodiment 1 to about 30 carbon atoms, and in one embodiment 1 to about 20 carbon atoms. In one embodiment, each R is independently methyl, ethyl, propyl, isopropyl, n-butyl, isobutyl, amyl, 4-methyl-2-pentyl, isooctyl, decyl, dodecyl, tetradecyl, 2-pentenyl, dodecenyl, phenyl, naphthyl, alkylphenyl, alkylnaphthyl, phenylalkyl, naphthylalkyl, alkylphenylalkyl or alkylnaphthylalkyl.

In one embodiment, the organic sulfide is a compound represented by the formula:

$$R\text{—}C(O)\text{—}S\text{—}(S)_n\text{—}C(O)\text{—}R \qquad (E\text{-}III)$$

wherein in Formula (E-III), R and n are as defined above, with compounds wherein n is 1 being especially useful.

In one embodiment, the organic sulfide is a compound represented by the formula

$$RO\text{—}C(S)\text{—}S\text{—}(S)_n\text{—}C(S)\text{—}OR \qquad (E\text{-}IV)$$

wherein in Formula (E-IV), R and n are as defined above, with compounds wherein n is 1 being useful.

In one embodiment, the organic sulfide is a compound represented by the formula

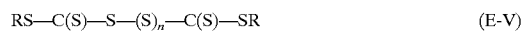
$$RS\text{—}C(S)\text{—}S\text{—}(S)_n\text{—}C(S)\text{—}SR \qquad (E\text{-}V)$$

wherein in Formula (E-V), R and n are as defined above, with compounds wherein n is 1 being especially useful.

In one embodiment, the organic sulfide is a compound represented by the formula

$$RRN\text{—}C(S)\text{—}S\text{—}(S)_n\text{—}C(S)\text{—}NRR \qquad (E\text{-}VI)$$

wherein in Formula (E-VI), R and n are as defined above, with compounds wherein n is 1 being especially useful.

These compounds are known and can be prepared by conventional techniques. For example, an appropriate mercaptan, alcohol or amine can first be reacted with an alkali metal reagent (e.g., NaOH, KOH) and carbon disulfide to form the corresponding thiocarbonate or dithiocarbamate. The thiocarbonate or dithiocarbamate is then reacted with an oxidizing agent (e.g., hydrogen peroxide, cobalt maleonitriledithioate, $K_2Fe(CN)_6$, $FeCl_3$, dimethylsulfoxide, dithiobis(thioformate), copper sulfate, etc.) to form a disulfide, or with sulfur dichloride or sulfur monochloride to form a trisulfide or tetrasulfide, respectively. The oxygen-containing analogs of these compounds wherein $X^1$ and $X^2$ in Formula (E-I) are oxygen can be prepared by treating the sulfur-containing compounds with water or steam.

The mercaptans that can be used include the hydrocarbyl mercaptans represented by the formula R-S-H, wherein R is as defined above in Formula (E-I). In one embodiment, R is an alkyl, an alkenyl, cycloalkyl, or cycloalkenyl group. R may be an aryl (e.g., phenyl, naphthyl), alkylaryl, arylalkyl or alkylaryl alkyl group. R may also be a haloalkyl, hydroxyalkyl, or hydroxyalkyl-substituted (e.g., hydroxymethyl, hydroxyethyl, etc.) aliphatic group. In one embodiment, R contains from about 2 to about 30 carbon atoms, or from about 2 to about 24, or from about 3 to about 18 carbon atoms. Examples include butyl mercaptan, amyl mercaptan, hexyl mercaptan, octyl mercaptan, 6-hydroxymethyloctanethiol, nonyl mercaptan, decyl mercaptan, 10-amino-dodecanethiol, dodecyl mercaptan, 10-hydroxymethyl-tetradecanethiol, and tetradecyl mercaptan.

Alcohols used to prepare the organic sulfides of Formula (E-I) can be any of those described above under the subtitle "(A) Mixed Polysulfides."

The amines that can be used include those described above under the subtitles "(A) Mixed Polysulfides" and "(B) Acylated Nitrogen-Containing Compounds."

The following examples illustrate the preparation of organic sulfides (E) that are useful with this invention.

EXAMPLE E-1

Di-n-butylamine (129 grams, 1 equivalent) is charged to a reactor. Carbon disulfide (8.4 grams, 1.1 equivalents) is added dropwise over a period of 2.5 hours. The resulting reaction is exothermic but the temperature of the reaction mixture is maintained below 50° C. using an ice bath. After the addition of carbon disulfide is complete the mixture is maintained at room temperature for one hour with stirring. A 50% aqueous sodium hydroxide solution (40 grams) is added and the resulting mixture is stirred for one hour. A 30% aqueous hydrogen peroxide solution (200 grams) is added dropwise. The resulting reaction is exothermic but the temperature of the reaction mixture is maintained below 50° C. using an ice bath. The mixture is transferred to a separatory funnel. Toluene (800 grams) is added to the mixture. The organic layer is separated from the product and washed with one liter of distilled water. The separated and washed organic layer is dried over sodium carbonate and filtered through diatomaceous earth. The mixture is stripped on a rotary evaporator at 77° C. and 20 mm Hg to provide the desired dithiocarbamate disulfide product which is in the form of a dark orange liquid.

EXAMPLE E-2

Di-n-butyl amine (1350 grams) is charged to a reactor. Carbon disulfide (875 grams) is added dropwise while maintaining the mixture below 50° C. A 50% aqueous sodium hydroxide solution (838 grams) is added dropwise. A 30% aqueous $H_2O_2$ solution (2094 grams) is added dropwise. The reaction mixture exotherms. An aqueous layer and an organic layer form. The aqueous layer is separated from the organic layer. Diethyl ether (1000 grams) is mixed with the aqueous layer to extract organic material from it. The diethyl ether containing extract is added to the organic layer. The resulting mixture is stripped at 70° C. and 20 mm Hg, and then filtered through diatomaceous earth to provide the desired disulfide product which is in the form of a brown liquid.

EXAMPLE E-3

A mixture of 1-octanethiol (200 grams), 50% aqueous NaOH solution (110 grams) and toluene (200 grams) is prepared and heated to reflux (120° C.) to remove water. The mixture is cooled to room temperature and carbon disulfide (114.5 grams) is added. A 30% aqueous $H_2O_2$ solution (103 grams) is added dropwise while maintaining the temperature below 50° C. Diethyl ether is added and then extracted. The organic layer is isolated, washed with distilled water, dried and chromotographed using hexane to provide the desired disulfide product which is in the form of a yellow liquid.

EXAMPLE E-4

(a) A mixture of 4000 grams of dodecyl mercaptan, 1600 grams of a 50% aqueous NaOH solution and 2000 grams of toluene is prepared and heated to 125° C. to remove 1100 grams of water. The reaction mixture is cooled to 40° C. and 1672 grams of carbon disulfide are added. The mixture is heated to 70° C. and maintained at that temperature for 8 hours. The mixture is filtered using diatomaceous earth and stripped at 100° C. and 20 mm Hg to form the desired product which is in the form of a red liquid.

(b) 200 grams of the product from part (a) and 200 grams of hexane are placed in a reactor and cooled to 10° C. 130 grams of a 30% aqueous $H_2O_2$ solution are added dropwise while maintaining the temperature below 45° C. The mixture is extracted with diethyl ether. The organic portion is washed with water, dried with $Na_2CO_3$, filtered, and heated under azeotropic conditions to remove water and provide the desired disulfide product which is in the form of a bright red liquid.

EXAMPLE E-5

1700 grams of methylpentanol and 407 grams of potassium hydroxide are placed in a reactor. The mixture is heated under reflux conditions to remove 130–135 grams of water. The mixture is cooled to 50° C., and 627 grams of carbon disulfide are added. 750 grams of a 30% aqueous $H_2O_2$ solution are added dropwise. The mixture exotherms, and an aqueous layer and an organic layer are formed. The aqueous layer is separated from the organic layer. The organic layer is stripped at 100° C. and 20 mm Hg and filtered to provide the desired disulfide product which is in the form of an orange liquid.

EXAMPLE E-6

1100 grams of methylpentyl alcohol and 863 grams of a 50% aqueous NaOH solution are placed in a reactor and heated to 120° C. to remove 430 grams of water. The mixture is cooled to 50° C. and 925 grams of carbon disulfide are added. 623 grams of a 30% aqueous $H_2O_2$ solution are added dropwise. The resulting reaction is exothermic, and an aqueous and an organic layer are formed. The aqueous layer is separated. The organic layer is stripped at 100° C. and 20 mm Hg and filtered to provide the desired disulfide product.

Lubricating Compositions and Functional Fluids.

The lubricating compositions and functional fluids of the present invention are based on diverse oils of lubricating viscosity, including natural and synthetic lubricating oils and mixtures thereof. The lubricating compositions may be lubricating oils and greases useful in industrial applications and in automotive engines, transmissions and axles. These lubricating compositions are effective in a variety of applications including crankcase lubricating oils for spark-ignited and compression-ignited internal combustion engines, including automobile and truck engines, two-cycle engines, aviation piston engines, marine and low-load diesel engines, and the like. Also, automatic transmission fluids, farm tractor fluids, transaxle lubricants, gear lubricants, metal-working lubricants, hydraulic fluids, and other lubricating oil and grease compositions can benefit from the incorporation of the compositions of this invention. The inventive lubricating compositions are particularly effective as engine lubricating oils having enhanced antiwear properties.

The lubricant compositions of this invention employ an oil of lubricating viscosity which is generally present in a major amount (i.e. an amount greater than about 50% by weight). Generally, the oil of lubricating viscosity is present in an amount greater than about 60%, or greater than about 70%, or greater than about 80% by weight of the composition.

The natural oils useful in making the inventive lubricants and functional fluids include animal oils and vegetable oils (e.g., castor oil, lard oil) as well as mineral lubricating oils such as liquid petroleum oils and solvent treated or acid-treated mineral lubricating oils of the paraffinic, naphthenic or mixed paraffinic-naphthenic types. Oils of lubricating viscosity derived from coal or shale are also useful. Synthetic lubricating oils include hydrocarbon oils such as polymerized and interpolymerized olefins (e.g., polybutylenes, polypropylenes, propylene-isobutylene copolymers, etc.); poly(1-hexenes), poly-(1 -octenes), poly (1-decenes), etc. and mixtures thereof; alkylbenzenes (e.g., dodecyl-benzenes, tetradecylbenzenes, dinonylbenzenes, di-(2-ethylhexyl)benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc., constitute another class of known synthetic lubricating oils that can be used. These are exemplified by the oils prepared through polymerization of ethylene oxide or propylene oxide, the alkyl and aryl ethers of these polyoxyalkylene polymers (e.g., methyl-polyisopropylene glycol ether having an average molecular weight of about 1000, diphenyl ether of polyethylene glycol having a molecular weight of about 500–1000, diethyl ether of polypropylene glycol having a molecular weight of about 1000–1500, etc.) or mono- and polycarboxylic esters thereof, for example, the acetic acid esters, mixed $C_{3-8}$ fatty acid esters, or the $C_{13}$Oxo acid diester of tetraethylene glycol.

Another suitable class of synthetic lubricating oils that can be used comprises the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.) Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl)silicate, tetra-(4-methylhexyl)silicate, tetra-(p-tert-butylphenyl) silicate, hexyl-(4-methyl-2-pentoxy) disiloxane, poly(methyl) siloxanes, poly-(methylphenyl) siloxanes, etc.). Other synthetic lubricating oils include liquid esters of phosphorus-containing acids (e.g., tricresyl phosphate, trioctyl phosphate, diethyl ester of decanephosphonic acid, etc.), polymeric tetrahydrofurans and the like.

Unrefined, refined and refined oils, either natural or synthetic (as well as mixtures of two or more of any of these) of the type disclosed hereinabove can be used in the lubricants of the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to those skilled in the art such as solvent extraction, secondary distillation, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

In one embodiment, component (A) is employed in the lubricant or functional fluid at a concentration in the range of about 0.001% to about 5% by weight, and in one embodiment about 0.01% to about 3%, and in one embodiment about 0.02% to about 2% by weight based on the total weight of the lubricant or functional fluid. In one embodiment, component (B) is employed in the lubricant or functional fluid at a concentration in the range of about 0.01% to about 20% by weight, and in one embodiment from about 0.1% to about 10%, and in one embodiment from about 0.5% to about 10% by weight based on the total weight of the lubricant or functional fluid. In one embodiment, component (C) is employed in the lubricant or functional fluid at a concentration in the range of up to about 20% by weight, and in one embodiment from about 0.01 % to about 10%, and in one embodiment from about 0.05% to about 5% by weight based on the total weight of the lubricant or functional fluid. In one embodiment, component (D) is employed in the lubricant or functional fluid at a concentration in the range of up to about 10% by weight, and in one embodiment about 0.01% to about 5%, and in one embodiment about 0.1% to about 3% by weight based on the total weight of the lubricant or functional fluid. In one embodiment, component (E) is employed in the lubricant or functional fluid at a concentration in the range of up to about 10% by weight, and in one embodiment about 0.001% to about 5% by weight, and in one embodiment about 0.01% to about 3%, and in one embodiment about 0.02% to about 2% by weight based on the total weight of the lubricant or functional fluid.

In one embodiment the inventive lubricating compositions are useful as engine lubricating oils or crankcase oils.

These compositions may be characterized by a phosphorus content of up to about 0.12% by weight, and in one embodiment up to about 0.11% by weight, and in one embodiment up to about 0.10% by weight, and in one embodiment up to about 0.09% by weight, and in one embodiment up to about 0.08% by weight, and in one embodiment up to about 0.05% by weight. In one embodiment the phosphorus content is in the range of about 0.01% to about 0.12% by weight, and in one embodiment about 0.01 % to about 0.10% by weight, and in one embodiment about 0.02% to about 0.09% by weight and in one embodiment about 0.05% to about 0.09% by weight.

When used for crankcase applications such as for gasoline and diesel engines, the oil of lubricating viscosity can be selected to provide an SAE crankcase viscosity number of 5W, 10W, 20W or 30W grade lubricants. The lubricating compositions may also have a so-called multigrade rating such as SAE 10W-30, 10W-40, 10W-50, etc. Multigrade lubricants may include a minor viscosity improving amount of a viscosity improver which is formulated with the oil of lubricating viscosity to provide the above lubricant grades. Useful viscosity improvers include polyolefins, such as polybutylene; rubbers, such as styrene-butadiene or styrene-isoprene; or polyacrylates, such as polymethacrylates. Useful viscosity improvers that are available commercially include Acryloid viscosity improvers available from Rohm & Haas; Shellvis rubbers available from Shell Chemical; and Lubrizol 3174 available from The Lubrizol Corporation.

In one embodiment, the inventive lubricating compositions and functional fluids are used as gear oils. When used as such gear oils the use of phosphorus-containing extreme pressure and/or antiwear agents other than component (A) of this invention is reduced or eliminated. These gear oil compositions generally contain less than about 0.5%, or less than about 0.25%, or less than about 0.1% by weight phosphorus, and in one embodiment, less than about 0.05% by weight phosphorus.

In one embodiment, the oil of lubricating viscosity is selected to provide a lubricating composition having a kinematic viscosity of at least about 3.5, or at least about 4.0 cSt at 100° C. In one embodiment, the oil of lubricating viscosity is selected to provide a lubricating composition of at least an SAE gear oil viscosity number of about 60 or about 65, more preferably about SAE 75. The lubricating composition may also have a so-called multigrade rating such as SAE 60W-80, 65W-80, 65 W-90, 75W-80, 75W-90, 80W-90, 80W-140 or 85W-140.

The invention also provides for the use of lubricants and functional fluids containing other additives in addition to components (A), (B), (C), (D) and (E). Such additives include, for example, detergents and dispersants, corrosion-inhibiting agents, antioxidants, viscosity improving agents, extreme pressure (E.P.) agents, pour point depressants, friction modifiers, fluidity modifiers, anti-foam agents, etc.

The inventive lubricating compositions and functional fluids can contain one or more detergents or dispersants of the ash-producing or ashless type. The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

Ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art, and any of them are suitable for use in the lubricant compositions and functional fluids of this invention. The following are illustrative:

(1) Reaction products of carboxylic acids (or derivatives thereof) containing at least about 34 and preferably at least about 54 carbon atoms with nitrogen containing compounds such as amine, organic hydroxy compounds such as phenols and alcohols, and/or basic inorganic materials. Examples of these "carboxylic dispersants" are described in many U.S. Pat. Nos. including 3,219,666; 4,234,435; and 4,938,881.

(2) Reaction products of relatively high molecular weight aliphatic or alicyclic halides with amines, preferably oxyalkylene polyamines. These may be characterized as "amine dispersants" and examples thereof are described for example, in the following U.S. Pat. Nos. 3,275,554; 3,438,757; 3,454,555; and 3,565,804.

(3) Reaction products of alkyl phenols in which the alkyl group contains at least about 30 carbon atoms with aldehydes (especially formaldehyde) and amines (especially polyalkylene polyamines), which may be characterized as "Mannich dispersants." The materials described in the following U.S. Pat. Nos. are illustrative: 3,649,229; 3,697,574; 3,725,277; 3,725,480; 3,726,882; and 3,980,569.

(4) Products obtained by post-treating the amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Pat. Nos. 3,639,242; 3,649,229; 3,649,659; 3,658,836; 3,697,574; 3,702,757; 3,703,536; 3,704,308; and 3,708,422.

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. Pat. Nos. 3,329,658; 3,449,250; 3,519,565; 3,666,730; 3,687,849; and 3,702,300.

The above-noted patents are incorporated by reference herein for their disclosures of ashless dispersants.

The inventive lubricating compositions and functional fluids can contain one or more extreme pressure, corrosion inhibitors and/or oxidation inhibitors in addition to those that would be considered as being within the scope of the above-discussed components. Extreme pressure agents and corrosion- and oxidation-inhibiting agents which may be included in the lubricants and functional fluids of the invention are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; metal thiocarbamates, such as zinc dioctyidithiocarbamate, and barium heptylphenyidithiocarbamate; dithiocarbamate esters from the reaction product of dithiocarbamic acid and acrylic, methacrylic, maleic, fumaric or itaconic esters; dithiocarbamate containing amides prepared from dithiocarbamic acid and an acrylamide; alkylene-coupled dithiocarbamates; sulfur-coupled dithiocarbamates. Many of the above-mentioned extreme pressure agents and oxidation-inhibitors also serve as antiwear agents.

Pour point depressants are a useful type of additive often included in the lubricating oils and functional fluids described herein. The use of such pour point depressants in oil-based compositions to improve low temperature properties of oil-based compositions is well known in the art. See, for example, page 8 of "Lubricant Additives" by C. V. Smallheer and R. Kennedy Smith (Lezius Hiles Co. publishers, Cleveland, Ohio, 1967). Examples of useful pour point depressants are polymethacrylates; polyacrylates; polyacrylamides; condensation products of haloparaffin waxes and aromatic compounds; vinyl carboxylate polymers; and terpolymers of dialkylfumarates, vinyl esters of fatty acids and alkyl vinyl ethers. A specific pour point depressant that can be used is the product made by alkylating naphthalene with polychlorinated paraffin and $C_{16}$–$C_{18}$ alpha-olefin. Pour point depressants useful for the purposes of this invention, techniques for their preparation and their uses are described in U.S. Pat. Nos. 2,387,501; 2,015,748; 2,655,479; 1,815,022; 2,191,498; 2,666,746; 2,721,877; 2,721,878; and 3,250,715 which are herein incorporated by reference for their relevant disclosures.

Anti-foam agents are used to reduce or prevent the formation of stable foam. Typical anti-foam agents include silicones or organic polymers. Additional antifoam compositions are described in "Foam Control Agents," by Henry T. Kemer (Noyes Data Corporation, 1976), pages 125–162.

Each of the foregoing additives, when used, is used at a functionally effective amount to impart the desired properties to the lubricant or functional fluid. Thus, for example, if an additive is a dispersant, a functionally effective amount of this dispersant would be an amount sufficient to impart the desired dispersancy characteristics to the lubricant or functional fluid. Similarly, if the additive is an extreme-pressure agent, a functionally effective amount of the extreme-pressure agent would be a sufficient amount to improve the extreme-pressure characteristics of the lubricant or functional fluid. Generally, the concentration of each of these additives, when used, ranges from about 0.001% to about 20% by weight, and in one embodiment about 0.01% to about 10% by weight based on the total weight of the lubricant or functional fluid.

The lubricant compositions of the present invention may be in the form of lubricating oils or greases in which any of the above-described oils of lubricating viscosity can be employed as a vehicle. Where the lubricant is to be used in the form of a grease, the lubricating oil generally is employed in an amount sufficient to balance the total grease composition and generally, the grease compositions will contain various quantities of thickening agents and other additive components of the type described above to provide desirable properties. Generally, the greases will contain from about 0.01 to about 20–30% of such additive components.

A wide variety of thickening agents can be used in the preparation of the greases of this invention. Included among the thickening agents are alkali and alkaline earth metal soaps of fatty acids and fatty materials having from about 12 to about 30 carbon atoms. The metals are typified by sodium, lithium, calcium and barium. Examples of fatty materials include stearic acid, hydroxy stearic acid, stearin, oleic acid, palmetic acid, myristic acid, cottonseed oil acids, and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Useful thickening agents employed in the grease compositions are essentially hydrophilic in character, but which have been converted into a hydrophobic condition by the introduction of long chain hydrocarbon radicals onto the surface of the clay particles prior to their use as a component of a grease composition, as, for example, by being subjected to a preliminary treatment with an organic cationic surface-active agent, such as an onium compound. Typical onium compounds are tetraalkylammonium chlorides, such as dimethyl dioctadecyl ammonium chloride, dimethyl dibenzyl ammonium chloride and mixtures thereof This method of conversion, being well known to those skilled in the art, and is believed to require no further discussion. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is generally employed in an amount from about 0.5 to about 30% by weight, and in one embodiment from about 3% to about 15% by weight of the total grease composition.

Component (A), and optional components (B) to (E) of the inventive compositions as well as one of the other above-discussed additives or other additives known in the art can be added directly to the lubricant or functional fluid. In one embodiment, however, they are diluted with a substantially inert, normally liquid organic diluent such as mineral oil, naphtha, benzene, toluene or xylene to form an additive concentrate which is then added to the base oil to form the lubricant or functional fluid. These concentrates usually contain from about 1% to about 99% by weight, and in one embodiment about 10% to about 90% by weight of component (A) and, optionally, one or more of components (B) to (E) as well as one or more other additives known in the art or described hereinabove. The remainder of the concentrate is the substantially inert normally liquid diluent.

The following Examples 1–20 illustrate lubricating compositions and functional fluids within the scope of the invention.

| | wt. % |
|---|---|
| Example 1 | |
| Product of Example A-1 | 0.5 |
| Base oil | Remainder |

-continued

| | wt. % |
|---|---|
| Example 2 | |
| Product of Example A-2 | 1.0 |
| Base oil | Remainder |
| Example 3 | |
| Product of Example A-3 | 1.4 |
| Base oil | Remainder |
| Example 4 | |
| Product of Example A-4 | 0.7 |
| Base oil | Remainder |
| Example 5 | |
| Product of Example A-5 | 2.0 |
| Base oil | Remainder |
| Example 6 | |
| Product of Example A-1 | 0.5 |
| Product of Example B-1 | 4.0 |
| Base oil | Remainder |
| Example 7 | |
| Product of Example A-2 | 1.5 |
| Product of Example B-2 | 5.0 |
| Base oil | Remainder |
| Example 8 | |
| Product of Example A-3 | 1.0 |
| Product of Example B-1 | 5.0 |
| Base oil | Remainder |
| Example 9 | |
| Product of Example A-4 | 0.3 |
| Product of Example B-2 | 4.5 |
| Base oil | Remainder |
| Example 10 | |
| Product of Example A-5 | 1.0 |
| Product of Example B-1 | 5.5 |
| Base oil | Remainder |
| Example 11 | |
| Product of Example A-1 | 1.1 |
| Product of Example B-2 | 6.5 |
| Base oil | Remainder |
| Example 12 | |
| Product of Example A-1 | 0.9 |
| Product of Example C-1 | 0.7 |
| Base oil | Remainder |
| Example 13 | |
| Product of Example A-1 | 0.8 |
| Product of Example C-3 | 1.4 |
| Base oil | Remainder |

-continued

| | wt. % |
|---|---|
| Example 14 | |
| Product of Example A-1 | 1.2 |
| Product of Example C-7 | 0.5 |
| Base oil | Remainder |
| Example 15 | |
| Product of Example A-1 | 1.2 |
| Product of Example D-1 | 0.6 |
| Base oil | Remainder |
| Example 16 | |
| Product of Example A-1 | 0.6 |
| Product of Example E-1 | 0.5 |
| Base oil | Remainder |
| Example 17 | |
| Product of Example A-1 | 1.5 |
| Product of Example B-1 | 4.5 |
| Product of Example C-1 | 0.5 |
| Base oil | Remainder |
| Example 18 | |
| Product of Example A-1 | 0.5 |
| Product of Example B-1 | 5.5 |
| Product of Example C-1 | 1.0 |
| Product of Example D-1 | 0.5 |
| Base oil | Remainder |
| Example 19 | |
| Product of Example A-1 | 1.0 |
| Product of Example B-1 | 5.5 |
| Product of Example C-1 | 0.5 |
| Product of Example D-1 | 0.25 |
| Product of Example E-1 | 0.25 |
| Base oil | Remainder |
| Example 20 | |
| Product of Example A-1 | 0.5 |
| Product of Example B-1 | 5.0 |
| Product of Example B-2 | 1.5 |
| Product of Example C-1 | 0.5 |
| Product of Example D-1 | 0.5 |
| Base oil | Remainder |

Examples 21–30 disclosed in Table I are provided for the purpose of further illustrating lubricating compositions and functional fluids within the scope of the invention. These compositions are useful as engine lubricating oil compositions. In Table I all numerical values, except for the concentration of the silicone antifoam agent, are in percent by weight. The concentration of the silicone antifoam agent is in parts per million, ppm.

TABLE I

| Example No. | 21 | 22 | 23 | 24 | 25 | 26 | 27 | 28 | 29 | 30 |
|---|---|---|---|---|---|---|---|---|---|---|
| Base oil (85% 100 N + 15% 150 N) | 82.0 | 82.25 | 82.0 | 82.25 | 82.0 | 82.25 | 82.0 | 82.25 | 82.0 | 82.25 |
| Product of Example A-1 | 0.5 | 0.25 | — | — | — | — | — | — | — | — |
| Product of Example A-2 | — | — | 0.5 | 0.25 | — | — | — | — | — | — |
| Product of Example A-3 | — | — | — | — | 0.5 | 0.25 | — | — | — | — |
| Product of Example A-4 | — | — | — | — | — | — | 0.5 | 0.25 | — | — |
| Product of Example A-5 | — | — | — | — | — | — | — | — | 0.5 | 0.25 |
| Product of Example B-1 | 4.0 | 4.0 | 4.0 | 4.0 | 4.0 | 4.0 | 4.0 | 4.0 | 4.0 | 4.0 |
| Product of Example B-2 | 1.4 | 1.4 | 1.4 | 1.4 | 1.4 | 1.4 | 1.4 | 1.4 | 1.4 | 1.4 |
| Product of Example C-1 | 0.7 | 0.7 | 0.7 | 0.7 | 0.7 | 0.7 | 0.7 | 0.7 | 0.7 | 0.7 |
| Overbased Mg sulfonate, metal/sulfonate ratio = 14.7, oil content = 42% | 0.45 | 0.45 | 0.45 | 0.45 | 0.45 | 0.45 | 0.45 | 0.45 | 0.45 | 0.45 |

TABLE I-continued

| Example No. | 21 | 22 | 23 | 24 | 25 | 26 | 27 | 28 | 29 | 30 |
|---|---|---|---|---|---|---|---|---|---|---|
| Overbased Ca sulfonate, metal/sulfonate ratio = 1.2, oil content = 50% | 0.2 | 0.2 | 0.2 | 0.2 | 0.2 | 0.2 | 0.2 | 0.2 | 0.2 | 0.2 |
| Overbased Na succinate, oil content = 49% | 0.2 | 0.2 | 0.2 | 0.2 | 0.2 | 0.2 | 0.2 | 0.2 | 0.2 | 0.2 |
| Ca overbased sulfur coupled alkyl phenol, oil content = 39% | 0.5 | 0.5 | 0.5 | 0.5 | 0.5 | 0.5 | 0.5 | 0.5 | 0.5 | 0.5 |
| Olefin copolymer VI improver | 0.7 | 0.7 | 0.7 | 0.7 | 0.7 | 0.7 | 0.7 | 0.7 | 0.7 | 0.7 |
| Alkylated diphenylamine | 0.5 | 0.5 | 0.5 | 0.5 | 0.5 | 0.5 | 0.5 | 0.5 | 0.5 | 0.5 |
| Polymethacrylate pour point depressant | 0.2 | 0.2 | 0.2 | 0.2 | 0.2 | 0.2 | 0.2 | 0.2 | 0.2 | 0.2 |
| Sulfur monochloride reacted with alpha olefin mixture followed by contact with sodium disulfide | 0.25 | 0.25 | 0.25 | 0.25 | 0.25 | 0.25 | 0.25 | 0.25 | 0.25 | 0.25 |
| Vegetable oil | 0.1 | 0.1 | 0.1 | 0.1 | 0.1 | 0.1 | 0.1 | 0.1 | 0.1 | 0.1 |
| Diluent oil | 8.4 | 8.4 | 8.4 | 8.4 | 8.4 | 8.4 | 8.4 | 8.4 | 8.4 | 8.4 |
| Silicone antifoam agent, ppm | 18 | 18 | 18 | 18 | 18 | 18 | 18 | 18 | 18 | 18 |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A lubricant or functional fluid comprising a major amount of an oil of lubricating viscosity and a minor amount of at least one compound represented by the formula $$T^1T^2-P(X^1)-(S)_n-S-C(X^2)-L^1 \quad \text{(A-I)}$$

wherein in Formula (A-I):

$T^1$ and $T^2$ are independently R, SR or OR;

$L^1$ is R, SR, OR or NRR;

$X^1$ and $X^2$ are independently O or S;

each R is independently a hydrocarbyl group; and n is 1 to 4.

2. The lubricant or functional fluid of claim 1 wherein in Formula (A-I), $T^1$ and $T^2$ are each OR, $X^1$ is S, and n is 1 or 2.

3. The lubricant or functional fluid of claim 1 wherein in Formula (A-I), $T^1$ and $T^2$ are each SR, $X^1$ is S, and n is 1 or 2.

4. The lubricant or functional fluid of claim 1 wherein in Formula (A-I), $X^2$ is S, $L^1$ is SR, and n is 1 or 2.

5. The lubricant or functional fluid of claim 1 wherein in Formula (A-I), $X^2$ is S, $L^1$ is OR, and n is 1 or 2.

6. The lubricant or functional fluid of claim 1 wherein in Formula (A-I), $X^2$ is S, $L^1$ is NRR, and n is 1 or 2.

7. The lubricant or functional fluid of claim 1 wherein in Formula (A-I), n is 1.

8. The lubricant or functional fluid of claim 1 further comprising one or more of:

a compound represented by the formula $$T^3T^4-P(X^3)-(S)_n-S-(DMTD)-S-J \quad \text{(A-II)}$$

and a compound represented by the formula $$L^2-C-(X^4)-(S)_n-S-(DMTD)-S-G \quad \text{(A-III)}$$

wherein:

DMTD is a thiadiazole nucleus;

J is H, SR, $-S-P(X^5)-T^5T^6$ or $-S-C(X^6)-L^3$;

G is H, SR or $-S-C(X^7)-L^4$;

$T^3$, $T^4$, $T^5$, and $T^6$ are independently R, SR, or OR;

$L^2$, $L^3$ and $L^4$ are independently R, SR, OR, or NRR;

$X^3$, $X^4$, $X^5$, $X^6$, and $X^7$ are independently O or S;

each R is independently a hydrocarbyl group; and n is 1 to 4.

9. The lubricant or functional fluid of claim 1 further comprising:

(B) an acylated nitrogen-containing compound having a substituent of at least about 10 aliphatic carbon atoms.

10. The lubricant or functional fluid of claim 9 wherein (B) is derived from a substituted succinic acid or anhydride and at least one alkylene polyamine, the substituent groups on said succinic acid or anhydride being derived from polybutene in which at least about 50% of the total units derived from butenes are derived from isobutylene, said polybutene being characterized by an $\overline{M}n$ value of about 1500 to about 2000 and an $\overline{M}w/\overline{M}n$ value of about 3 to about 4, said acid or anhydride being characterized within its structure of an average of about 1.5 to about 2.5 succinic groups for each equivalent weight of substituent groups.

11. The lubricant or functional fluid of claim 9 wherein (B) is derived from a substituted succinic acid or anhydride and at least one alkylene polyamine, the substituent groups on said succinic acid or anhydride being derived from polybutene in which at least about 50% of the total units derived from butenes are derived from isobutylene, said polybutene being characterized by an $\overline{M}n$ value of about 800 to about 1200 and an $\overline{M}w/\overline{M}n$ value of about 2 to about 3, said acid or anhydride being characterized within its structure of an average of about 0.9 to about 1.2 succinic groups for each equivalent weight of substituent groups.

12. The lubricant or functional fluid of claim 1 further comprising:

(C) a phosphorus compound other than (A-I).

13. The lubricant or functional fluid of claim 12 wherein (C) is a compound represented by the formula

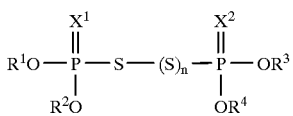

(C-IV)

wherein in Formula (C-IV), $R^1$, $R^2$, $R^3$ and $R^4$ are independently hydrocarbyl groups, $X^1$ and $X^2$ are independently O or S, and n is zero to 3.

14. The lubricant or functional fluid of claim 12 wherein (C) is a phosphorus acid, phosphorus acid ester, phosphorus acid salt, or derivative thereof.

15. The lubricant or functional fluid of claim 12 wherein (C) is a compound represented by the formula

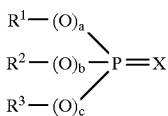

(C-I)

wherein in Formula (C-I), $R^1$, $R^2$ and $R^3$ are independently hydrogen or hydrocarbyl groups, X is O or S, and a, b and c are independently zero or 1.

16. The lubricant or functional fluid of claim 12 wherein (C) is a compound represented by the formula

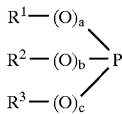

(C-II)

wherein in Formula (C-II), $R^1$, $R^2$ and $R^3$ are independently hydrogen or hydrocarbyl groups, and a, b and c are independently zero or 1.

17. The lubricant or functional fluid of claim 12 wherein (C) is a compound represented by the formula

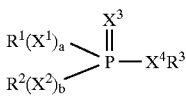

(C-III)

wherein in Formula (C-III): $X^1$, $X^2$ and $X^3$ and $X^4$ are independently O or S, and $X^1$ and $X^2$ can be $NR^4$; a and b are independently zero or 1; and $R^1$, $R^2$, $R^3$ and $R^4$ are independently hydrocarbyl groups, and $R^3$ and $R^4$ can be hydrogen; or a metal, amine or ammonium salt of said compound represented by Formula (C-III).

18. The lubricant or functional fluid of claim 17 wherein said compound represented by Formula (C-III) is a metal salt, said metal being a Group IA, IIA or IIB metal, aluminum, tin, iron, cobalt, lead, molybdenum, manganese, nickel, antimony, bismuth, or a mixture of two or more thereof.

19. The lubricant or functional fluid of claim 17 wherein said compound represented by Formula (C-III) is a metal salt, said metal being zinc.

20. The lubricant or functional fluid of claim 1 further comprising:

(D) a compound represented by the formula

(D-I)

wherein in Formula (D-I), $R^1$, $R^2$, $R^3$ and $R^4$ are independently hydrogen or hydrocarbyl groups, provided that at least one of $R^1$ and $R^2$ is a hydrocarbyl group; X is O or S; a is 1 or 2, provided that when a is 2, each $CR^3R^4$ can be the same or different; and Z is a hydrocarbyl group, a hetero group, a hydroxy hydrocarbyl group, an activating group, or a $-(S)C(X)NR^1R^2$ group; provide that when a is 2, Z is an activating group.

21. The lubricant or functional fluid of claim 20 wherein (D) is a compound represented by the formula

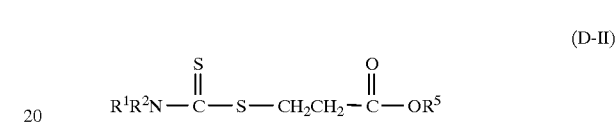

(D-II)

wherein in Formula (D-II), $R^1$, $R^2$ and $R^5$ are independently hydrocarbyl groups.

22. The lubricant or functional fluid of claim 20 wherein (D) is a compound represented by the formula

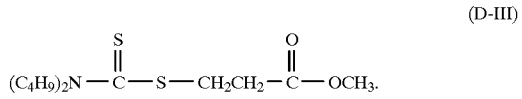

(D-III)

23. The lubricant or functional fluid of claim 1 further comprising:

(E) a compound represented by the formula

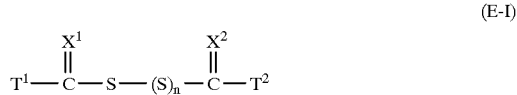

(E-I)

wherein in Formula (E-I), $T^1$ and $T^2$ are independently R, OR, SR or NRR wherein each R is independently a hydrocarbyl group, $X^1$ and $X^2$ are, independently O or S, and n is zero to 3.

24. The lubricant or functional fluid of claim 1 further comprising a corrosion-inhibiting agent, detergent, dispersant, antioxidant, viscosity improving agent, antiwear agent, extreme-pressure agent, pour-point depressant, friction-modifier, fluidity-modifier, anti-foam agent, or mixture of two or more thereof.

25. The lubricant of functional fluid of claim 1 in the form of an engine lubricating oil.

26. A method for lubricating an internal combustion engine comprising supplying to such engine the engine lubricating oil of claim 25.

27. The lubricant or functional fluid of claim 1 in the form of a gear oil.

28. The lubricant of functional fluid of claim 1 in the form of a grease.

29. A process for making a lubricant or a functional fluid comprising mixing an oil of lubricating viscosity with at least one compound represented by the formula

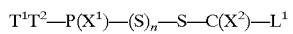
(A-I)
wherein in Formula (A-I):
T$^1$ and T$^2$ are independently R, SR or OR;
L$^1$ is R, SR, OR or NRR;
X$^1$ and X$^2$ are independently O or S;
each R is independently a hydrocarbyl group; and
n is 1 to 4.
* * * * *